(12) United States Patent
Venkataraman et al.

(10) Patent No.: US 10,716,544 B2
(45) Date of Patent: Jul. 21, 2020

(54) SYSTEM FOR 3D MULTI-PARAMETRIC ULTRASOUND IMAGING

(71) Applicant: ZMK Medical Technologies Inc., Grass Valley, CA (US)

(72) Inventors: Rajesh Venkataraman, Rocklin, CA (US); Saradwata Sakar, Newcastle, CA (US); Xu Yang, Nevada City, CA (US); Michael Ahmadi, Durham, NC (US); Pablo Medina, Grass Valley, CA (US)

(73) Assignee: ZMK MEDICAL TECHNOLOGIES INC., Grass Valley, CA (US)

( * ) Notice: Subject to any disclaimer, the term of this patent is extended or adjusted under 35 U.S.C. 154(b) by 211 days.

(21) Appl. No.: 15/695,630

(22) Filed: Sep. 5, 2017

(65) Prior Publication Data

US 2018/0008237 A1 Jan. 11, 2018

Related U.S. Application Data

(63) Continuation-in-part of application No. 15/289,425, filed on Oct. 10, 2016, now Pat. No. 10,441,250.

(Continued)

(51) Int. Cl.
*A61B 8/08* (2006.01)
*A61B 8/12* (2006.01)
(Continued)

(52) U.S. Cl.
CPC ............ *A61B 8/5246* (2013.01); *A61B 8/06* (2013.01); *A61B 8/08* (2013.01); *A61B 8/12* (2013.01);
(Continued)

(58) Field of Classification Search
CPC .......... A61B 8/00; A61B 8/12; A61B 8/4218; A61B 8/4245
(Continued)

(56) References Cited

U.S. PATENT DOCUMENTS 5,170,790 A 12/1992 Lacoste et al.
5,224,175 A 6/1993 Gouge et al.
(Continued)

FOREIGN PATENT DOCUMENTS

WO 2000014668 3/2000
WO 2006089426 8/2006
(Continued)

*Primary Examiner* — Jon Eric C Morales
(74) *Attorney, Agent, or Firm* — Snell & Wilmer L.L.P.; Russell T. Manning

(57) ABSTRACT

Systems and methods are disclosed that facilitate obtaining two dimensional (2D) ultrasound images, using two or more ultrasound imaging modes or modalities, to generate 2D multi-parametric ultrasound (mpUS) images and/or to generate a three-dimensional (3D) mpUS image. The different ultrasound imaging modes acquire images in a common frame of reference during a single procedure to facilitate their registration. The mpUS images (i.e., 2D or 3D) may be used for enhanced and/or automated detection of one or more suspicious regions. After identifying one or more suspicious regions, the mpUS images may be utilized with a real-time image to guide biopsy or therapy the region(s). All these processes may be performed in a single medical procedure.

7 Claims, 19 Drawing Sheets

Related U.S. Application Data

(60) Provisional application No. 62/238,836, filed on Oct. 8, 2015.

(51) Int. Cl.

| | | |
|---|---|---|
| *A61B 8/00* | (2006.01) | |
| *G06T 7/00* | (2017.01) | |
| *G01S 7/52* | (2006.01) | |
| *A61B 8/06* | (2006.01) | |
| *G01S 15/89* | (2006.01) | |

(52) U.S. Cl.
CPC .......... *A61B 8/4218* (2013.01); *A61B 8/4263* (2013.01); *A61B 8/4461* (2013.01); *A61B 8/463* (2013.01); *A61B 8/469* (2013.01); *A61B 8/481* (2013.01); *A61B 8/485* (2013.01); *A61B 8/488* (2013.01); *A61B 8/5207* (2013.01); *A61B 8/54* (2013.01); *G01S 7/52042* (2013.01); *G01S 7/52071* (2013.01); *G01S 15/894* (2013.01); *G06T 7/0012* (2013.01); *G01S 7/52039* (2013.01); *G01S 15/899* (2013.01); *G01S 15/8993* (2013.01); *G06T 2207/10136* (2013.01); *G06T 2207/20081* (2013.01); *G06T 2207/30081* (2013.01)

(58) Field of Classification Search
USPC ........................................................ 600/437
See application file for complete search history.

(56) References Cited

U.S. PATENT DOCUMENTS

| | | |
|---|---|---|
| 5,230,623 A | 7/1993 | Guthrie et al. |
| 5,282,472 A | 2/1994 | Companion et al. |
| 5,320,101 A | 6/1994 | Faupel et al. |
| 5,383,454 A | 1/1995 | Bucholz |
| 5,398,690 A | 3/1995 | Batten et al. |
| 5,454,371 A | 10/1995 | Fenster et al. |
| 5,494,039 A | 2/1996 | Onik et al. |
| 5,531,520 A | 7/1996 | Grimson et al. |
| 5,562,095 A | 10/1996 | Downey et al. |
| 5,611,000 A | 3/1997 | Szeliski et al. |
| 5,810,007 A | 9/1998 | Holupka et al. |
| 5,824,007 A | 10/1998 | Faraz et al. |
| 5,842,473 A | 12/1998 | Finster et al. |
| 6,046,727 A | 4/2000 | Rosenberg et al. |
| 6,092,059 A | 7/2000 | Straforini et al. |
| 6,171,249 B1 | 1/2001 | Chin et al. |
| 6,179,262 B1 | 1/2001 | Ellard et al. |
| 6,238,342 B1 | 5/2001 | Feleppa et al. |
| 6,246,200 B1 | 6/2001 | Blumenkranz et al. |
| 6,251,072 B1 | 6/2001 | Ladak et al. |
| 6,261,234 B1 | 7/2001 | Lin |
| 6,298,148 B1 | 10/2001 | Cline et al. |
| 6,301,989 B1 | 10/2001 | Brown et al. |
| 6,325,760 B1 | 12/2001 | Takanori et al. |
| 6,334,847 B1 | 1/2002 | Fenster et al. |
| 6,342,891 B1 | 1/2002 | Fenster et al. |
| 6,351,660 B1 | 2/2002 | Burke et al. |
| 6,360,027 B1 | 3/2002 | Hossack et al. |
| 6,378,376 B1 | 4/2002 | Derman et al. |
| 6,385,332 B1 | 5/2002 | Zahalka et al. |
| 6,423,009 B1 | 7/2002 | Downey et al. |
| 6,425,865 B1 | 7/2002 | Salcudean et al. |
| 6,447,447 B1 | 9/2002 | Mitsumori |
| 6,447,477 B2 | 9/2002 | Burney et al. |
| 6,451,027 B1 | 9/2002 | Cooper et al. |
| 6,500,123 B1 | 12/2002 | Holloway et al. |
| 6,561,980 B1 | 5/2003 | Gheng et al. |
| 6,567,687 B2 | 5/2003 | Front et al. |
| 6,610,013 B1 | 8/2003 | Fenster et al. |
| 6,611,615 B1 | 8/2003 | Christensen |
| 6,620,111 B2 | 9/2003 | Stephens et al. |
| 6,674,916 B1 | 1/2004 | Deman et al. |
| 6,675,032 B2 | 1/2004 | Chen et al. |
| 6,675,211 B1 | 1/2004 | Mamaghani et al. |
| 6,689,065 B2 | 2/2004 | Aksnes et al. |
| 6,778,690 B1 | 8/2004 | Ladak et al. |
| 6,824,516 B2 | 11/2004 | Batten et al. |
| 6,842,638 B1 | 1/2005 | Suri et al. |
| 6,852,081 B2 | 2/2005 | Sumanaweera et al. |
| 6,909,792 B1 | 6/2005 | Carrott et al. |
| 6,931,745 B2 | 8/2005 | Granger |
| 6,952,211 B1 | 10/2005 | Cote et al. |
| 6,985,612 B1 | 1/2006 | Hahn |
| 7,004,904 B2 | 2/2006 | Chalana et al. |
| 7,008,373 B2 | 3/2006 | Stoianovici et al. |
| 7,039,216 B2 | 5/2006 | Shum et al. |
| 7,039,239 B2 | 5/2006 | Loui et al. |
| 7,043,063 B1 | 5/2006 | Noble et al. |
| 7,095,890 B2 | 8/2006 | Paragois et al. |
| 7,108,660 B2 | 9/2006 | Stephens et al. |
| 7,119,810 B2 | 10/2006 | Sumanaweera et al. |
| 7,139,601 B2 | 11/2006 | Bucholz et al. |
| 7,148,895 B2 | 12/2006 | Konishi et al. |
| 7,155,316 B2 | 12/2006 | Sutherland et al. |
| 7,162,065 B2 | 1/2007 | Ladak et al. |
| 7,167,760 B2 | 1/2007 | Dawant et al. |
| 7,189,246 B2 | 3/2007 | Otsuka et al. |
| 7,225,012 B1 | 5/2007 | Susil et al. |
| 7,255,310 B2 | 8/2007 | Niwa et al. |
| 7,274,811 B2 | 9/2007 | Sirohey et al. |
| 7,287,310 B2 | 10/2007 | Zuzelo |
| 7,302,092 B1 | 11/2007 | Fenster et al. |
| 7,403,646 B2 | 7/2008 | Sato |
| 7,412,776 B2 | 8/2008 | Iikubo et al. |
| 7,804,989 B2 | 9/2010 | Suri et al. |
| 7,832,114 B2 | 11/2010 | Suri et al. |
| 7,856,130 B2 | 12/2010 | Suri et al. |
| 7,875,039 B2 | 1/2011 | Vohra et al. |
| 7,942,060 B2 | 5/2011 | Suri et al. |
| 7,942,829 B2 | 5/2011 | Miller et al. |
| 8,064,664 B2 | 11/2011 | Suri et al. |
| 8,175,350 B2 | 5/2012 | Suri et al. |
| 8,278,913 B2 | 10/2012 | Kumar et al. |
| 8,425,418 B2 | 4/2013 | Suri et al. |
| 8,444,543 B2 | 5/2013 | Fenster et al. |
| 8,571,277 B2 | 10/2013 | Suri et al. |
| 8,788,019 B2 | 7/2014 | Downey et al. |
| 8,899,125 B2 | 12/2014 | Bax et al. |
| 9,070,190 B2 | 6/2015 | Gardi et al. |
| 9,113,816 B2 | 8/2015 | Kumar et al. |
| 9,131,922 B2 | 9/2015 | Li et al. |
| 2003/0000535 A1 | 1/2003 | Galloway, Jr. et al. |
| 2003/0135115 A1 | 7/2003 | Burdette et al. |
| 2004/0210133 A1 | 10/2004 | Nir |
| 2005/0075536 A1 | 4/2005 | Otsuka et al. |
| 2005/0159676 A1 | 7/2005 | Taylor et al. |
| 2005/0190189 A1 | 9/2005 | Chefd'hotel et al. |
| 2005/0197977 A1 | 9/2005 | Buck et al. |
| 2005/0243087 A1 | 11/2005 | Aharon |
| 2005/0249398 A1 | 11/2005 | Khamene et al. |
| 2006/0002601 A1 | 1/2006 | Fu et al. |
| 2006/0002630 A1 | 1/2006 | Fu et al. |
| 2006/0013482 A1 | 1/2006 | Dawant et al. |
| 2006/0036162 A1 | 2/2006 | Shahidi et al. |
| 2006/0079771 A1 | 4/2006 | Nir |
| 2006/0197837 A1 | 9/2006 | Flath et al. |
| 2006/0227131 A1 | 10/2006 | Schiwietz et al. |
| 2006/0258933 A1 | 11/2006 | Ellis et al. |
| 2007/0014446 A1 | 1/2007 | Sumanaweera et al. |
| 2007/0040830 A1 | 2/2007 | Papageorgiou |
| 2007/0116339 A1 | 5/2007 | Shen |
| 2007/0116381 A1 | 5/2007 | Khamene |
| 2007/0189603 A1 | 8/2007 | Kasperkiewicz et al. |
| 2007/0201611 A1 | 8/2007 | Pratx et al. |
| 2007/0270687 A1 | 11/2007 | Gardi et al. |
| 2008/0000448 A1 | 1/2008 | Bax et al. |
| 2008/0002870 A1 | 1/2008 | Farag et al. |
| 2008/0004481 A1 | 1/2008 | Bax et al. |
| 2008/0051648 A1 | 2/2008 | Suri et al. |
| 2008/0123910 A1 | 5/2008 | Zhu |
| 2008/0123927 A1 | 5/2008 | Miga et al. |

(56) References Cited

U.S. PATENT DOCUMENTS

| | | |
|---|---|---|
| 2008/0001616 A1 | 7/2008 | Suri et al. |
| 2008/0170770 A1 | 7/2008 | Suri et al. |
| 2008/0018637 A1 | 8/2008 | Shen et al. |
| 2008/0247616 A1 | 10/2008 | Pescatore et al. |
| 2008/0249403 A1* | 10/2008 | Suri ............ A61B 8/12 600/437 |
| 2009/0004851 A1 | 2/2009 | Suri et al. |
| 2009/0093715 A1 | 4/2009 | Downey et al. |
| 2009/0022787 A1 | 9/2009 | Suri et al. |
| 2009/0023436 A1 | 9/2009 | Bax et al. |
| 2009/0226065 A1 | 9/2009 | Chen |
| 2009/0032404 A1 | 12/2009 | Narayanan et al. |
| 2009/0032636 A1 | 12/2009 | Li et al. |
| 2009/0032655 A1 | 12/2009 | Vohra et al. |
| 2010/0000199 A1 | 1/2010 | Shen et al. |
| 2010/0000452 A1 | 1/2010 | Wei et al. |
| 2010/0001671 A1 | 1/2010 | Kumar et al. |
| 2010/0017255 A1 | 1/2010 | Gramza et al. |
| 2010/0098306 A1 | 4/2010 | Madabhushi et al. |
| 2010/0020794 A1 | 8/2010 | Zhao |
| 2011/0008105 A1 | 4/2011 | Zeng |
| 2011/0018468 A1 | 7/2011 | Li et al. |
| 2012/0008755 A1 | 4/2012 | Miller et al. |
| 2014/0012167 A1 | 5/2014 | Bax et al. |
| 2017/0002055 A1 | 1/2017 | Xu et al. |
| 2017/0023160 A1 | 8/2017 | Venkataraman et al. |

FOREIGN PATENT DOCUMENTS

| | | |
|---|---|---|
| WO | 2007045810 | 4/2007 |
| WO | 2007137179 | 11/2007 |
| WO | 2007147232 | 12/2007 |
| WO | 2008024992 | 2/2008 |
| WO | 2008057850 | 5/2008 |
| WO | 2008062346 | 5/2008 |
| WO | 2008083225 | 7/2008 |
| WO | 2008121773 | 10/2008 |
| WO | 2008124138 | 10/2008 |
| WO | 2008124284 | 10/2008 |
| WO | 2017007875 | 1/2017 |

* cited by examiner

2D Image Storage

3D Volume Image

SYSTEM FOR 3D MULTI-PARAMETRIC ULTRASOUND IMAGING

CROSS REFERENCE

The present application is a continuation-in-part of U.S. patent application Ser. No. 15/289,425 having a filing date of Oct. 10, 2016, which issued as U.S. Pat. No. 10,441,250 on Oct. 15, 2019, and which claims the benefit of the filing date of U.S. Provisional Application No. 62/238,836 having a filing date of Oct. 8, 2015, the entire contents of both of which are incorporated herein by reference.

FIELD

The present disclosure pertains to the field of medical imaging, and more particularly to the registration of multiple modalities of ultrasound images to generate enhanced contrast between tissue structures for diagnosis and therapy. In one application, multiple modalities of ultrasound images are coregistered into a multimodal ultrasound image to aid urologists in finding target sites for biopsy and/or therapy of a prostate.

BACKGROUND

Medical imaging, including X-ray, magnetic resonance (MR), computed tomography (CT), ultrasound, and various combinations of these techniques are utilized to provide images of internal patient structure for diagnostic purposes as well as for interventional procedures. One application of medical imaging (e.g., 3-D imaging) is in the detection and/or treatment of prostate cancer. According to the National Cancer Institute (NCI), a man's chance of developing prostate cancer increases drastically from 1 in 10,000 before age 39 to 1 in 45 between 40 to 59 and 1 in 7 after age 60. The overall probability of developing prostate cancer from birth to death is close to 1 in 6.

Traditionally either elevated Prostate Specific Antigen (PSA) level or Digital Rectal Examination (DRE) has been widely used as the standard for prostate cancer detection. For a physician to diagnose prostate cancer, a biopsy of the prostate must be performed. This is done on patients that have either high PSA levels or an irregular digital rectal exam (DRE), or on patients that have had previous negative biopsies but continue to have elevated PSA. Biopsy of the prostate requires that a number of tissue samples (i.e., cores) be obtained from various regions of the prostate. For instance, the prostate may be divided into six regions (i.e., sextant biopsy), apex, mid and base bilaterally, and one representative sample is randomly obtained from each sextant. Such random sampling continues to be the most commonly practiced method although it has received criticism in recent years on its inability to sample regions where there may be significant volumes of malignant tissues resulting in high false negative detection rates. Further using such random sampling it is estimated that the false negative rate is about 30% on the first biopsy. 3-D Transrectal Ultrasound (TRUS) guided prostate biopsy is a commonly used method to guide biopsy when testing for prostate cancer, mainly due to its ease of use and low cost.

Recently, it has been suggested that TRUS guidance may also be applicable for targeted focal therapy (TFT). In this regard, adoption of TFT for treatment of prostate cancer has been compared with the evolution of breast cancer treatment in women. Rather than perform a radical mastectomy, lumpectomy has become the treatment of choice for the majority of early-stage breast cancer cases. Likewise, some commentators believe that accurate targeting and ablation of cancerous prostate tissue (i.e., TFT) may eventually replace prostatectomy and/or whole gland treatment as the first choice for prostate treatment. Such targeted treatment has the potential to alleviate side effects of current treatment including, incontinence and/or impotence. Such commentators typically agree that the ability to visualize malignant or cancerous tissue during treatment will be of importance to achieve the accuracy of targeting necessary to achieve satisfactory results.

While TRUS provides a convenient platform for real-time guidance for either biopsy or therapy, it is believed that some malignant tissues can be isoechoic in TRUS. That is, differences between malignant cells and surrounding healthy tissue may not be discernable in a standard ultrasound image. Accordingly, using a standard TRUS image a sole means of guidance has not allowed for visually identifying potentially malignant tissue. Further, speckle and shadows make ultrasound images difficult to interpret, and many cancers are often undetected even after saturation biopsies that obtain several (>20) needle samples. To improve the identification of potentially cancerous regions for biopsy or therapy procedures, it has been proposed to combine different pre-acquired imaging modalities (e.g., MRI, CT etc.), which may provide improved tissue contrast, with a live TRUS image during biopsy or therapy.

Imaging modalities like computed tomography (CT) and magnetic resonance imaging (MRI) can provide information that previously could not be derived from standard TRUS imaging alone. While CT lacks good soft tissue contrast to help detect abnormalities within the prostate, it can be helpful in finding extra-capsular extensions when soft tissue extends to the periprostatic fat and adjacent structures, and seminal vesicle invasions. MRI is generally considered to offer the best soft tissue contrast of all imaging modalities. Both anatomical (e.g., $T_1$, $T_2$) and functional MRI, e.g. dynamic contrast-enhanced (DCE), magnetic resonance spectroscopic imaging (MRSI) and diffusion-weighted imaging (DWI) can help visualize and quantify regions of the prostate based on specific attributes. Stated otherwise, such different imaging modalities may allow for locating suspect regions or lesions within the prostate even when such regions/lesions are isoechoic.

Unfortunately, use of pre-acquired images, from different imaging modalities, with a live TRUS image provides a number of logistic problems. Specifically, use of other different imaging modalities such as MRI has required a patient to attend a separate procedure during which images of the other imaging modality are acquired. Once such images are acquired, (e.g., an MRI or CT image) such images must be registered with a live TRUS image acquired during a biopsy or therapy procedure. Registration of images obtained from different modalities creates a number of complications. This is especially true in soft tissue applications where the shape of an object in two images may change between acquisitions of each image. Further, in the case of prostate imaging the frame of reference (FOR) of the acquired images is typically different. That is, multiple MM volumes are obtained in high resolution transverse, coronal or sagittal planes respectively. These planes are usually in rough alignment with the patient's head-toe, anterior-posterior or left-right orientations. In contrast, TRUS images are often acquired while a patient lies on his side in a fetal position by reconstructing multiple rotated samples 2D frames to a 3D volume. The 2D image frames are obtained at various instances of rotation of the TRUS probe after insertion in to the rectal canal. The probe is inserted at an angle (approximately 30-45 degrees) to the patient's head-toe orientation. As a result the gland in MM and TRUS will need to be rigidly aligned because their relative orientations are unknown at scan time. Also the two glands would have to be compensated for the different gland shapes (non-rigid alignment) due to various factors like bladder filling, pressure of the ultrasound probe on the prostate, etc. It is against this background that the presented inventions have been developed.

SUMMARY

Aspects of the presented inventions are based on the recognition that, while desirable for diagnosis and treatment, use of different pre-acquired images from different imaging techniques (e.g., MRI) has a number of drawbacks as previously noted. Accordingly, the present inventor has recognized that it would be desirable to provide a multi-parameter image from an ultrasound device during a single imaging and biopsy/treatment session to reduce or eliminate multiple visits and/or registration errors arising from use of differing imaging techniques. More specifically, provided herein is a multi-parametric ultrasound (mpUS) system that operates similar to multi-parameter MRI in that it looks to extract contrast between tissue structures by imaging the different physiological behavior of the gland. Along these lines, the multi-parametric ultrasound system may incorporate standard B-mode ultrasound images, ultrasound elastography images, Doppler ultrasound imaging, and/or perfusion (e.g., contrast) imaging using micro bubbles to name a few. Each of these different imaging modalities are available on various high-end ultrasound machines, but unlike an MRI machine there has not been a way to standardize the protocols between different users, centers and ultrasound machines. Each parametric image/map in ultrasound has its difficulties arising from the fact that the most common ultrasound transducers provide only 2D images and that they are done by hand which reduces the reliability of the results.

The presented systems and methods (i.e., utilities) are unique in that they can combine multiple 2D images (i.e., from a single ultrasound mode or multiple ultrasound modes) into a single 3D volume. In order to produce such a 3D volume, an ultrasound probe is held on a positioning device (e.g., manually adjustable arm or robotic arm) that provides control over where the probe is positioned for imaging (e.g., relative to a prostate). The positioning device allows obtaining multiple sets of 2D images or parametric maps in a common frame of reference. The utilities are further operative to fuse the multiple parametric maps or images automatically through mechanical registration, though software registration could be used if necessary.

With the probe in the positioning device and positioned proximate to the target tissue (e.g., prostate) the utilities are operable to perform any, all or any combination of the following:
1. Create a 3D B-mode volume from a set of 2D B-mode images
   a. Acquire a set of 2D B-mode images by rotating or moving the probe and reconstruct them into 3D volume
2. Create a 3D elastography volume from a set of 2D elastography images
   a. Acquire a set of 2D elastography (strain wave, shear wave or ARFI) images at each location of the probe before rotating or moving to the next location.
   b. Reconstruct from the acquired 2D images a 3D elastography volume
3. Create 3D+time volume from a set of 2D B-mode images before, during and after the injection of microbubbles as contrast agent.
   a. Acquire a set of 2D B-mode images by continuously rotating or moving the probe over a given time and combine them into a 3D volume for that time point.
   b. A time point is defined as the volume created from 2D B-mode images when the probe is rotated (or otherwise moves) from a start position to a finish position (e.g., 180 degrees from the start position).
   c. Keep combining the 2D B-mode images to get a set of 3D volumes over time.
   d. Apply the 2 compartments Tofts model (or any pharmacokinetic modeling or phenomenological modeling) to the 3D time series data to extract parametric maps
4. Create a 3D Doppler volume from a set of 2D Doppler images.
   a. Acquire a set of 2D Doppler images by rotating or moving the probe and reconstruct them to 3D volume.
5. Create a 3D PAT volume from a set of 2D PAT image.
   a. Acquire a set of 2D PAT image by rotating or moving the probe and reconstruct them to 3D volume Any or all of the 2D images and/or 3D volumes are acquired during a common procedure (e.g., sequentially) and are mechanically registered since the probe is supported in a fixed position by the positioning device with no movement other than rotational or axial movement of the probe (e.g., movement with a single degree of freedom). In one arrangement, the probe is rotated about an axis that runs through the acquisition portion of the probe thereby eliminating the distortion on the gland when rotating the probe. Also the rotation of the probe may be controlled by a motor further reducing registration offsets between the images. In any case, two or more images from two or more imaging modalities may be combined/registered to generate a mpUS image or map.

Based on all the mpUS images/maps, a computer aided detection algorithm or classifier may be applied to detect suspicious regions. The utility may then align the probe to the suspicious region to take a biopsy sample and/or apply therapy. That is, in one arrangement, the utility generates a multi-parametric ultrasound image, analyzes the image to detect suspicious region(s), and provides real-time images to guide biopsy and/or therapy to the suspicious region(s). In the case of prostate imaging/therapy, the utility does a 3D mpUS study of the prostate that will be used for automatic detection of one or more suspicious regions and then guides biopsy or therapy application the region(s) using the device in the same sitting. One uniqueness lies in the ability to standardize the mpUS settings over different ultrasound machines.

In one arrangement, a method is provided for generating a multiple parameter ultrasound image or composite image that includes anatomical features of tissue and blood flows in tissue of a patient. The method includes positioning an ultrasound probe proximate to the tissue of a patient. In one arrangement, a transrectal ultrasound probe is position proximate to a prostate of a patient. The ultrasound probe is supported by a positioning device such that once positioned, the probe may be rotated about an axis or linearly advanced along an axis without further distorting the tissue. The method includes acquiring a first set of ultrasound images (e.g., B-mode images) during a first movement of the ultrasound probe. The first set of images identify, at least, anatomical features of the tissue. The method further includes perfusing the tissue of the patient with an echogenic contrast agent. Once the tissue is perfused, the second set of ultrasound images may be acquired during a second movement of the ultrasound probe. The perfusion of the tissue allows the second set of ultrasound images (e.g., B-mode images) to identify blood flows within the tissue. The first and second sets of ultrasound images may then be registered to generate a composite ultrasound image including the anatomical features of the tissue and the blood flows within the tissue. Though both set of ultrasound images may be acquired utilizing the same imagining modality (B-mode) the two sets of ultrasound images are considered as different imaging modalities due to the introduction of the echogenic contrast agent. In one arrangement the echogenic contrast agent includes a plurality of microbubbles which are injected into the patient tissue (e.g., into a vascular system associated with the patient tissue).

In another arrangement, a method is provided for generating composite image of patient tissue including anatomical features of the tissue and tissue densities for the tissue. The method includes positioning an ultrasound probe proximate to the tissue of a patient. A first set of ultrasound images are acquired during a first movement of the probe relative to the tissue to identify anatomical features of the patient tissue. After the first set of images are acquired, a second set of ultrasound images are acquired during a second movement of the probe. During the second image acquisition, the vibration or other minor displacement is imparted onto the ultrasound probe, which is in contact with the patient tissue. This vibration or displacement results in minor vibrations within the tissue for determination of tissue elasticity. The vibratory movement/displacement of the probe typically results in a probe movement between a reference position and a displaced position. In such an arrangement, images may be acquired while the probe is in the reference position such that all images of the first set of images and second set of images are acquired from a common probe location. After the first and second set of ultrasound images are acquired, these ultrasound images are registered to generate a composite ultrasound image including the anatomical features of the tissue and elasticity of the tissue.

In a further arrangement, a method is provided for generating a multi-parameter or composite ultrasound image utilizing at least three imaging modalities. In this arrangement, an ultrasound probe is positioned proximate to patient tissue. Then in sequence, a first set of ultrasound images are acquired during a first rotation of the ultrasound probe, a second set of ultrasound images are acquired during a second rotation of the ultrasound probe and a third set of ultrasound images are acquired during a third rotation of the ultrasound probe. Importantly, each rotation of the ultrasound probe acquires images utilizing a different imaging modality. By way of example, a first imaging modality may be at a b-mode imaging modality. A second ultrasound imagining mode may be a B-mode ultrasound imaging modality in conjunction with vibrations imparted into the tissue (e.g., elastography ultrasound imaging modality). A third imagining modality may be contrast enhanced ultrasound imaging modality where, for instance, B-mode images are acquired after the perfusion of the tissue with an echogenic contrast agent. Once all three sets of images are acquired, these images are registered to generate the composite ultrasound image. In a further arrangement, a classifier may be applied to a portion of the composite/multi-parameter ultrasound image to identify one or more regions of interest.

According to another arrangement, an ultrasound medical imaging system is provided. The system includes a positioning device having a linkage where one end of the linkage is a free end that is operative to move in three dimensions and that is further configured to be locked in a fixed position. The system further includes an ultrasound probe holder that is attached to a rotational shaft of the free end of the linkage. Accordingly, an ultrasound probe may be supported by the ultrasound probe holder in a known alignment with a rotational axis of the rotational shaft. A rotary encoder is configured to generate angular output indicative of the angular orientation of the rotational shaft and hence a supported ultrasound probe. The system further includes an ultrasound system that is configured to acquire ultrasound images. Typically, the ultrasound system is configured to acquire ultrasound images in two or more imaging modalities, though this is not a strict requirement. A registration system is configured to receive angular outputs from the rotary encoder as well as ultrasound images from the ultrasound system. The registration system utilizes the angular outputs received in conjunction with each ultrasound image to register the ultrasound images into a common frame of reference. In one arrangement, the registration system is configured to receive a first set of ultrasound images acquired utilizing a first imaging modality and a second set of ultrasound images acquired utilizing a second ultrasound imaging modality. In any case, the registration system is configured to register these images together in a common frame of reference. These registered images (e.g., composite image) may then be output on a display.

In one embodiment of the present arrangement, rigid arms of the positioning device may further include encoders that generate positional outputs indicative of the position of the rigid arms. This allows for determining location of the free end of the linkage and hence a supported ultrasound probe in three-dimensional space. The encoders utilized for the linkages and/or the rotary encoder may be any sensor that is configured to provide an output indicative of, for example, an angular position of an arm and/or angular position of a rotational shaft.

In a further embodiment of the present arrangement, the system includes a motor for controllably rotating the rotational shaft. In such an embodiment, the system may further include a controller that is configured to control the motor to rotate the shaft to known angular positions in conjunction with acquiring ultrasound images. In such an embodiment, a first set of ultrasound images may be acquired having known spacing between each ultrasound image and a second set of ultrasound images may be acquired having the same angular spacing.

In a further embodiment of the present arrangement, the linkage may further include an actuator that is operative to impart a vibration or displacement to the rotational shaft and hence a supported ultrasound probe. Such vibration or displacement may be utilized to impart movement within the tissue for purposes of elastography imagining. In this embodiment, a controller may be utilized to control the displacement of the actuator and to acquire ultrasound images when the shaft is in a known (eg, reference) location.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging and therapy, it should be expressly understood that aspects of the present disclosure may be applicable to other medical imaging applications. In this regard, the following description is presented for purposes of illustration and description.

Systems and methods are disclosed that facilitate obtaining two dimensional (2D) ultrasound images, using two or more ultrasound imaging modes or modalities, to generate 2D multi-parametric ultrasound (mpUS) images and/or to generate a three-dimensional (3D) mpUS image. The different ultrasound imaging modes acquire images in a common frame of reference during a single procedure to facilitate their registration. That is, the acquired images are mechanically registered. The mpUS images (i.e., 2D or 3D) may be used for enhanced and/or automated detection of one or more suspicious regions. After identifying one or more suspicious regions, the mpUS images may be utilized with a real-time image to guide biopsy or therapy the region(s). All these processes may be performed in a single medical procedure.

Figure 1:
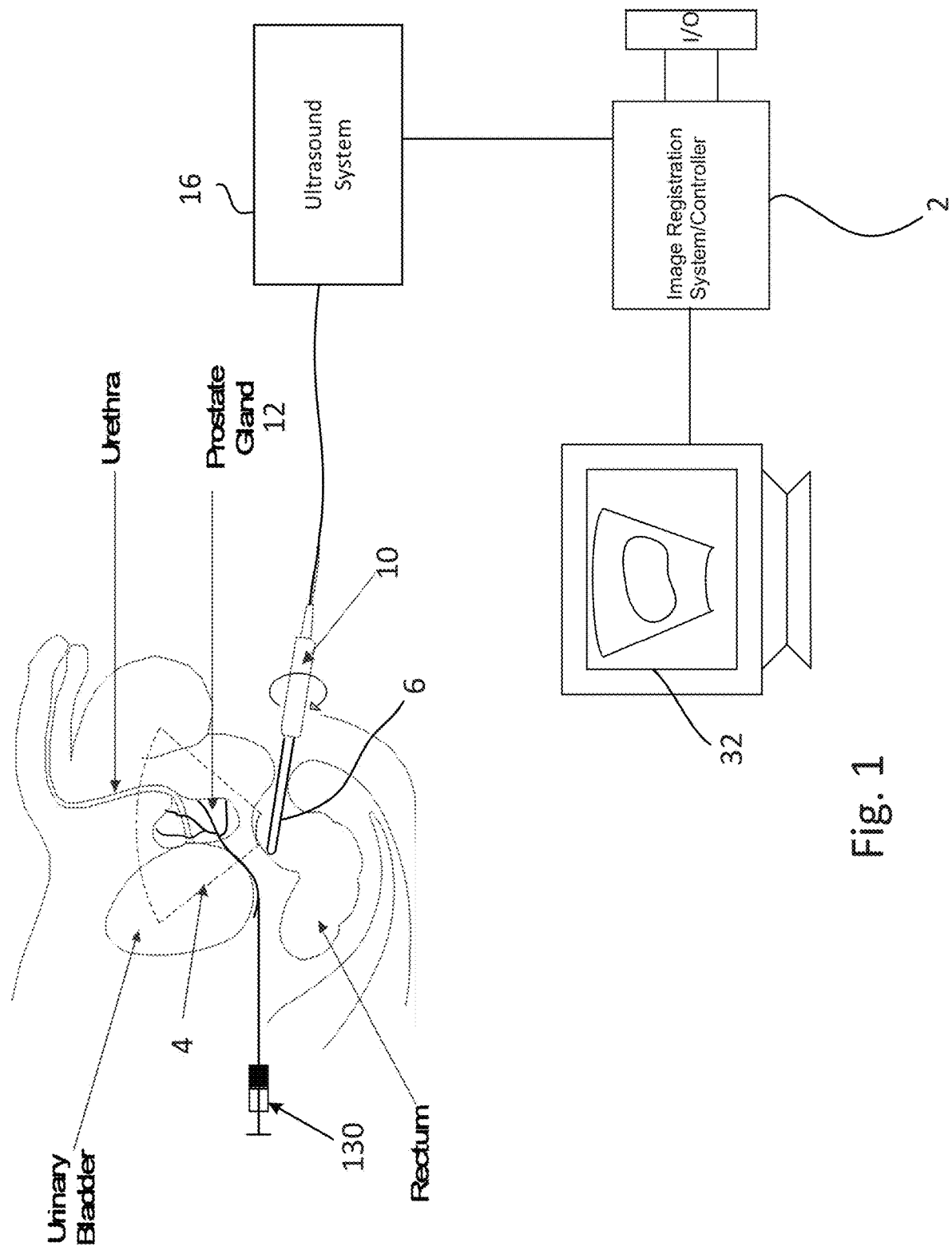
FIG. 1 shows a cross-sectional view of a trans-rectal ultrasound imaging system as applied to perform prostate imaging.

FIG. 1 illustrates a transrectal ultrasound transducer or probe 10 being utilized to obtain a plurality of 2D ultrasound images of the prostate 12. The ultrasound imaging system 16 connected to the probe 10 is a multi-parametric ultrasound system that is capable of obtaining ultrasound images/maps utilizing different imaging modalities. Non-limiting examples of such multi-modal ultrasound imaging systems include Hitachi Avius ultrasound, Flex focus ultrasound, and Siemens S3000 ultrasound. In the illustrated embodiment, the acquisition portion 6 and image plane 4 of the ultrasound probe 10 may be rotated through an arc (e.g., 180°) to acquire separate images of an area of interest using any one ultrasound imaging mode. The probe may be re-rotated to through the area of interest to acquire additional images using additional modes. In the present arrangement, the image(s) taken by the probe 10 are output from the ultrasound imaging system 16 to an image registration system 2, which may further output these images to a display 32. As more fully discussed herein, the imaging registration system is operative to register separate images ultrasound system 16 to generate composite images obtained in two or more different ultrasound modes.

Figure 2A:
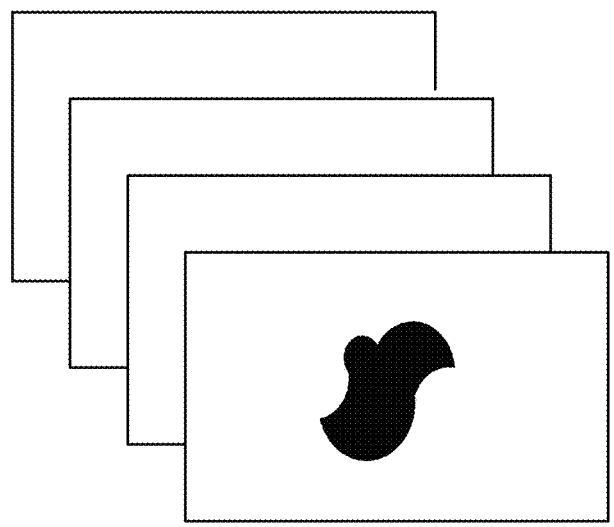
FIG. 2A illustrates two-dimensional images generated by the trans-rectal ultrasound imaging system of FIG. 1.
Figure 2B:
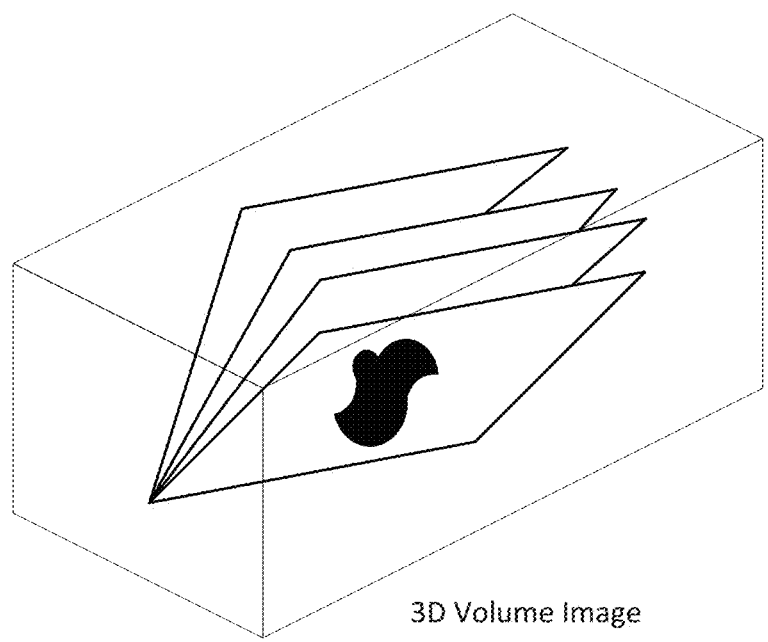
FIG. 2B illustrates a three-dimensional volume image generated from the two dimensional images of FIG. 2A.

The probe 10 may acquire plurality of individual images while being rotated over the area of interest. See FIGS. 2A-B. Each of these individual images may be represented as a 2D image. See FIG. 2A. Initially, such images may be in a polar or cylindrical coordinate system. In such an instance, it may be beneficial for processing to translate these images into a rectangular coordinate system. In any case, the 2-D images may be combined to generate a 3-D image. See FIG. 2B.

As shown in FIG. 1, the ultrasound probe 10 is a side-fire probe that generates ultrasound waves out of the side surface (e.g., acquisition axis). Other ultrasound probes may be utilized (e.g., end-fire). In any arrangement, it may be desirable to generate an image of patient tissue (e.g., the prostate 12) while the probe 10 remains positioned relative to the prostate. If there is little or no movement between acquisitions of the 2D images, these images may be readily registered together. If multiple ultrasound imaging modes are utilized, the image registration system 2 may register these images together to generate a composite 2D mpUS image and/or to generate a composite 3D mpUS image. However, manual manipulation of the probe 10 often results in relative and unaccounted movement between the probe and the prostate 12 between subsequent images. Accordingly, it is desirable to minimize relative movement between the probe 10 and the prostrate 12 for each image of each mode and between different imaging modalities. That is, it is desirable to eliminate precession, wobble or any other movement other than rotational movement of the probe about a fixed axis for image acquisition. It is also often desirable for probe 10 to remain fixed relative to the prostrate 12 during biopsy or other treatment procedures such that the desired tissue locations may be targeted accurately. To achieve such fixed positioning of probe 10, it is desirable to interface the probe 10 with a positioning device.

Figure 3:
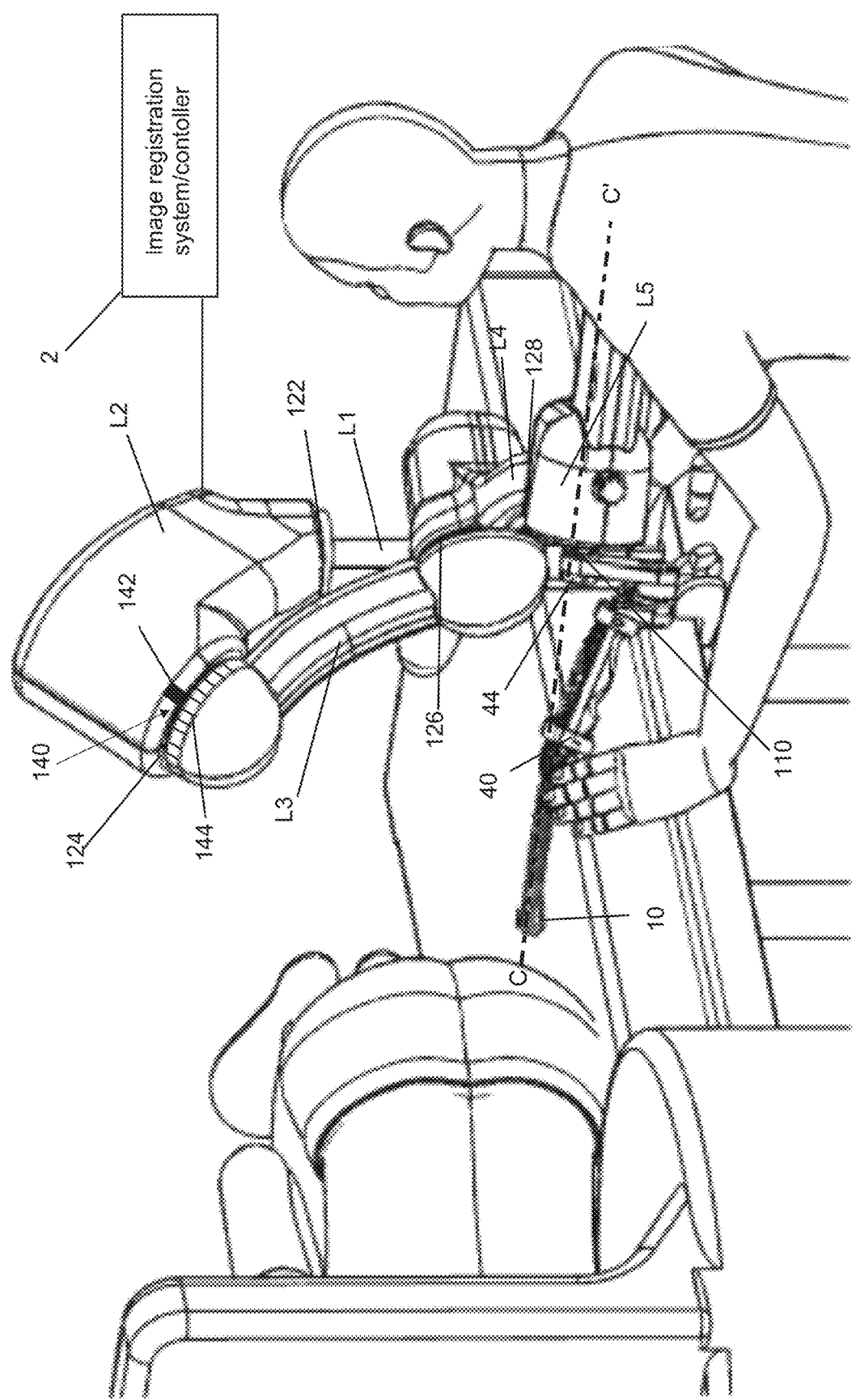
FIG. 3 illustrates use of a positioning device to position an ultrasound imaging device to perform prostate imaging.

An exemplary positioning device 100 shown in FIG. 3. The positioning device 100 maintains the acquisition axis of the probe 10 in a known position (e.g., fixed position for rotation about a rotational axis) relative to the prostate (or other target tissue) during image acquisition and provides location information (e.g., frame of reference information) to the image registration system 2 for use with each acquired image. Stated otherwise, in the present embodiment, the positioning device 100 maintains movement of an acquisition axis of the probe 10 to a single degree of freedom/movement about a rotational axis C-C' of the positioning device. Thus, all images taken from the probe are in a common frame of reference. In this regard, location outputs from the positioning device 100 may be supplied to the image registration system 2 to identify, for example the base location of each image plane and its angular position. Likewise, the output (e.g., images) from the probe 10 is provided by the ultrasound system to the image registration system 2, which may utilize this information to more accurately register the images and output (e.g., display) the imaged object (e.g., prostate). One exemplary positioning device is set forth in International Application Number PCT/CA2007/001076, entitled: Apparatus for Guiding a Medical Tool. Another exemplary positioning device is set forth in U.S. Pat. No. 7,832,114 entitled: Tracker Holder Assembly, the contents of both of which are fully incorporated herein by reference.

The positioning device 100 tracks the coordinates of the supported ultrasound probe 10 in 3D space and provides location information for the probe 10 to the connected image registration system 2. The positioning device 100 also measures the rotation of the probe 10 around the rotational axis C-C' such that the angular position of the imaging plane of the probe 10 is also provided to the imaging system. As shown in FIG. 3, the positioning device is composed of various linkages L1-L5 defined by rigid arms that are connected by rotating joints 122, 124, 126 and 128, which permit rotational motion between the linkages. Encoders between each joint 122, 124, 126 and 128 of the linkages L1-L5 are operative to provide an output indicative of the movement between those linkages. A probe support or cradle 40 is mounted to the rotational shaft 110 of the last linkage L5 of the positioning device 100 to engage and secure the ultrasound probe 10.

The five linkages L1-L5 of the exemplary positioning device permit movement in six degrees of freedom. However, it will be appreciated that differently configured positioning devices may be used and those devices may permit movement of a free end of the device with different degrees of freedom (e.g., three degrees of freedom). In the exemplary embodiment, the linkages of the positioning device 100 permit five degrees of motion for positioning the probe 10 relative to patient tissue and a sixth degree of motion around the rotational axis C-C'. Encoders 140 (only one shown on rotational joint 124 for clarity) measure rotational angle between each linkage L1-L5. That is, the encoders measure the rotation of the linkages about the various axes of the rotating joints 122-128. Geometric principles may then be used to compute tracking data (i.e., positional information) from the encoder measurements. The base link L1 defines a reference or base (e.g., reference axis/point of a global coordinate system) from which the position of the distal end (e.g., supported probe) of the assembly may be determined.

Connected to the end of the fourth linkage L4 is a cradle mounting linkage L5. The cradle mounting linkage L5 forms a free end of the linkage that may be positioned relative to patient tissue. More specifically, the cradle mounting linkage L5 includes a rotational shaft 110 to which the cradle 40 is mounted. See also FIG. 4A. Accordingly, once the cradle 40 is interconnected to the shaft 110, it may be positioned relative to patient tissue and rotated about the rotational axis C-C'. The rotational axis C-C' provides the sixth degree of freedom for the positioning device. In summary, the linkage assembly L1-L5 supports the probe 10 through rotating joint connections 122-128 while the cradle 40 supports the probe such that a longitudinal axis (e.g., acquisition axis) of the probe 10 is collinear with the rotational axis C-C'. Therefore, the angular position of the acquisition axis of the probe 10 relative to the base member and the global coordinate system may be determined. That is, the position of the probe 10 is determined by the angles between each pair of links L1-L5 in combination with the lengths of the links.

As noted, encoders 140 are used to measure the relative angles between each linkage L1-L5. The encoders for the positioning device 100 are incorporated into the various joints 122-128. In one arrangement, the encoders may be formed from off the shelf rotary encoders having a high accuracy. For instance, such accuracy may be 13 bits to provide 8,192 positions per revolution. One supplier of such rotary encoders is Renishaw Inc. of Chicago, Ill. However, it will be appreciated that other encoders including encoders produced by other manufacturers may be utilized as well. This accuracy in turn may determine the tracking accuracy of the positioning device 100.

Generally, the encoders 140 include a magnetic actuator 142 and a separate encoder body 144. In this regard, the magnetic actuator 142 (e.g., magnet) may be mounted to a shaft of the rotational axis that is disposed within an encoder body 144. In this regard, each joint may include a joint axel that includes a shaft and magnetic actuator. The joint axel may be received in cylindrical bores formed in the ends of the linkages. Such bores may include appropriate bushings, bearings etc. The encoder body may be mounted within the linkage (e.g., proximate to and/or around a rotational bore). In any case, the rotation of this magnet is sensed by an encoder chip and generates an output. As will be appreciated, each encoder will be interconnected to a computational device (e.g., imaging device, CPU, PC, etc.) utilizing appropriate connections, which are not shown in the present embodiment to simplify the illustration of the positioning device 100. In one arrangement, a commercial encoder interface (USB1, US digital) is used to read the encoder values. For example, a USB1 device may send data to a computer through a USB port and a DLL interface. The transformation between the image frame of reference and the ultrasound prober, may be performed. In any case, this allows for providing base frame of reference for use with the acquired images.

In addition to providing an output of the location of the distal end of the assembly, each of the joints 122-128 further includes a mechanical braking assembly (not shown). In this regard, once the positioning device 100 and probe 10 are positioned to a desired location (e.g., probe is positioned proximate to the prostate), these braking assemblies may be locked in order to maintain the positioning device 100 at a fixed position. At such time, the probe 10 may be rotated around the rotational axis C-C' to provide images having a fixed reference frame. In one arrangement, the braking mechanism simultaneously prevents the movement of the joints 122-128 and hence linkages L1-L5.

Figure 4A:
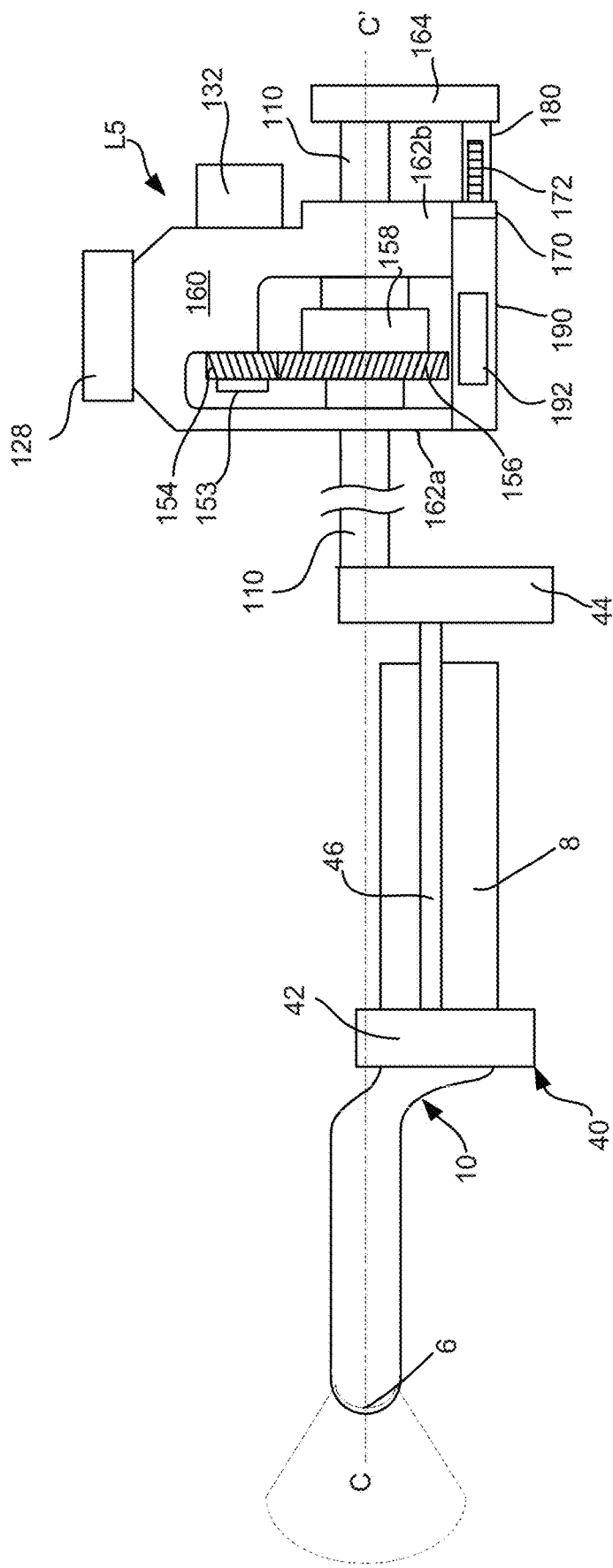
FIG. 4A illustrates a probe holding device and linkage assembly of the positioning device.

FIG. 4A illustrates one exemplary a holder assembly or cradle 40 that may be utilized to securely hold the ultrasound probe 10. The cradle 40 secures the probe 10 such that the geometry of the probe relative to the positioning device 100 is fixed. As shown, the cradle 40 includes a collar 42 that is adapted to be positioned about a handle portion 8 of an ultrasound probe 10. In this embodiment, the collar 42 defines an aperture having an inside surface tailored to match the outside surface of the handle of the probe. Once inserted into the cradle 40, relative movement between the probe and the cradle is entirely or substantially eliminated. In the exemplary embodiment, the collar 42 connects to a shaft connector 44 by first and second rods 46 (only one shown). These rods 46 extend along the handle portion 8 of the probe 10, when the probe is inserted within the collar 42. In the illustrated embodiment, the use of the rods allow a user to grasp the handle and/or rods such that a user may position the probe 10 relative to a patient. In this regard, the positioning device may be manually positioned by a user and locked in place when the probe is at a desired location. Alternatively, the positioning device may be fully automated (i.e., robotic). In such an embodiment, each of the joints 122-128 may further include an actuator/motor to control the movement of the linkages L1-L5.

The shaft connector 44 connects to the rotating shaft 110 of the positioning device 100. Accordingly, once the shaft connector 44 of the cradle 40 is connected to the shaft 110, the cradle and the probe 10 supported therein may be rotated around the rotational axis C-C' of the final linkage L5 of the positioning device 100. Importantly, the cradle is designed such that the rotational axis C-C' may be aligned, in a known orientation (e.g., passing perpendicular though the center of the end fire probe as illustrated), with the acquisition array 6 (e.g., transducer array axis) of the probe 10. Though one exemplary cradle is illustrated in FIG. 4, it will be appreciated that any cradle that affixes an acquisition array of the probe in a known orientation with the rotational axis C-C' of the positioning device may be utilized and that no limitation should be inferred from the disclosed embodiment. For instance, for a side fire probe, an acquisition axis of the side fire probe may be aligned with the rotational axis C-C'.

Once the cradle 40 interfaces with the shaft 110 of the positioning device, the supported probe 10 may be rotated about the fixed axis C-C'. In this regard, multiple images may be obtained from the supported probe 10 in different angular positions for image generation and registration (e.g., generating a 3-D image). As the probe is securely supported by the positioning device, there may be little or no probe movement, other than about the fixed axis of rotation, between successive images. Accordingly, successive images are mechanically registered to the common frame of reference.

Figure 4B:
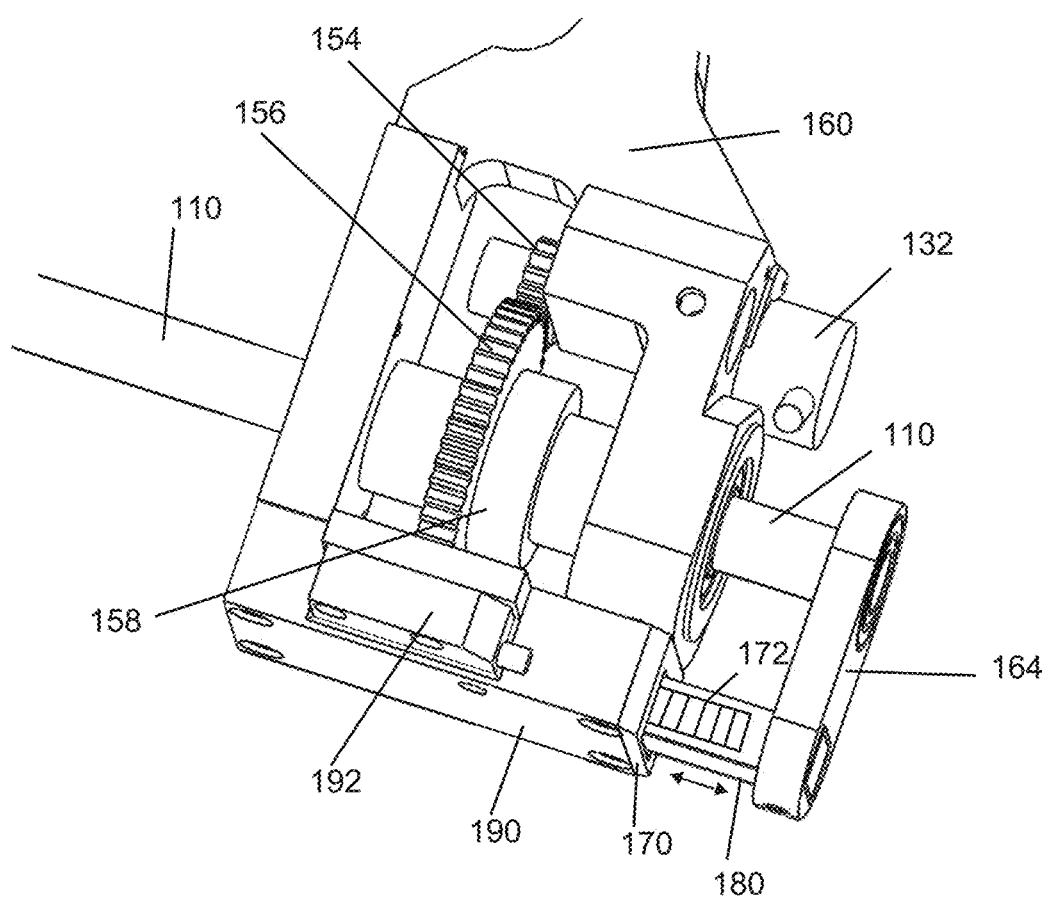
FIG. 4B illustrates a linkage assembly of the positioning device.
Figure 4C:
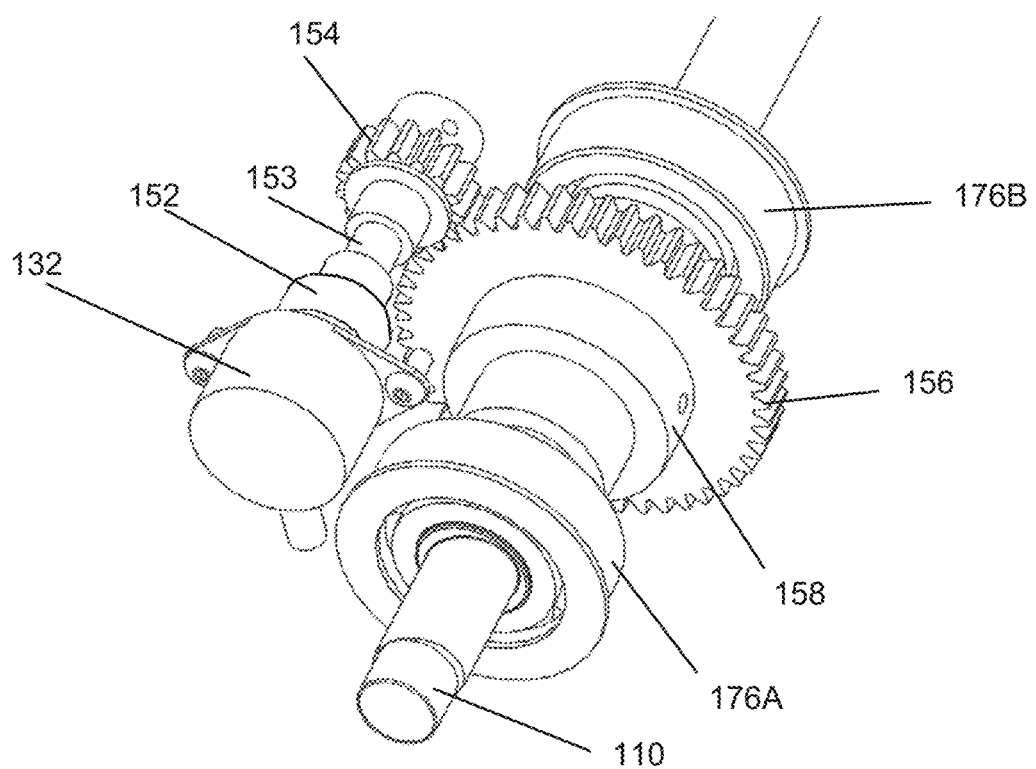
FIG. 4C illustrates a gear system of the linkage assembly

FIGS. 4A, 4B and 4C variously illustrate the last linkage L5 of the positioning device 100. The illustrated linkage L5 allows for the motorized rotation of the shaft 110, monitoring the angular rotation of the shaft 110, which supports the cradle 40 and probe 10, and monitoring the linear position of the shaft 110. The linkage L5 utilizes a motor 132 to controllably rotate the shaft 110 and, when attached, the supported cradle 40 and probe 10. In the illustrated embodiment, the motor is not directly connected to the shaft 110. Rather, a drive gear 154 mounted to the output shaft 153 of the motor 132 engages a driven gear 156 connected to the shaft 110, which supports the cradle 40. When assembled, the teeth of the drive gear 154 mesh and engage with the teeth on the driven gear 156. As will be appreciated, due to meshing between the gear teeth, rotation of the drive gear 154 rotates the driven gear 156. The linkage L5 utilizes a rotary encoder 152 that is operative to translate rotary motion of an output shaft 153 of a drive motor 132 into an electronic output that identifies the current angular position of the shaft 110. Accordingly, any rotary movement of the shaft 110 is accurately monitored by the rotary encoder 152.

The gears 154, 156 are disposed within a bracket 160 of the linkage L5. As illustrated, bores extend through first and second arms 162a, 162b of the bracket. These bores are sized to receive bearings 176a, 176b (See FIG. 4C) which support the shaft 110. (See FIG. 4). The shaft 110 passes through the bearings and through an aperture in the hub of 158 of the driven gear 156, which is disposed between the arms 162a, 162b. However, to permit axial movement of the shaft without moving the driven gear 156, the shaft 110 is adapted to slide through the hub of the driven gear 156 free of rotation. That is, the shaft 110 slides axially through the gear 156. However, rotation of the driven gear 156 rotates the shaft 110. In the present embodiment, this is accomplished by utilizing an ovular shaft 110 that fits within an ovular aperture through the hub 158 of the driven gear 156.

In this regard, it will be appreciated that the ovular shaft 110 may slide axially through the ovular aperture of the driven gear free of rotation. However, when the driven gear 156 is rotated by the drive gear 154, the shaft 110 turns. It will be appreciated that other arrangements may be utilized. For instance, the shaft 110 may be splined and fit through a splined hub within the driven gear 156. In any embodiment, when the motor 132 operates/actuates, the motor shaft 153 rotates the drive gear 154 and such rotation is translated to the driven gear 156 and shaft 110.

The linkage L5, also supports a linear positioning sensor 170. As shown in FIGS. 4A and 4B, the rearward end of the shaft 110 extends through the rearward arm 112a. A rearward end of the shaft 110 is received within a bushing or bearing within (e.g., press fit) a fixture 164, which connects to a linear slide or link bar 180. As shown, the rearward end of the link bar 180 is square such that the fixture 164 is angularly fixed relative to the link bar 180.

The link bar 180 extends through an actuator bracket 190 that is interconnected to the bottom of the bracket 160. More specifically, the actuator bracket 190 includes an aperture that is sized to permit the link bar 180 to pass there through. When the shaft 110 is advanced or retracted axially, this axial movement is transferred by the fixture 164 to the link bar 180, which then moves through the actuator bracket 160. The linear position of the shaft 110 and link bar 150 is measured utilizing a linear positioning sensor 170 (e.g., magnetic encoder), which is supported on an end of the actuator bracket 190 and is operative to read a magnetic strip 172 connected to the link bar. The linear position sensor includes a readhead that reads a magnetic position of a magnetic strip 172. As the magnetic strip moves relative to the readhead, the readhead detects the magnetic signature of the magnetized scale and processes these signals to generate a linear position output. Various different linear magnetic encoders are available, and one such encoder is available from RLS, a subsidiary of Renishaw PLC of Slovenia. However, it will be appreciated that other manufacturers exist and use of such linear magnetic encoders of such other manufacturers is envisioned. Such linear magnetic encoders may provide user selectable resolutions from 250 µm to 1 µm. In any case, when the shaft 110 is moved axially along its length, the link bar 180 and the supported strip 172 are correspondingly advanced or retracted.

The actuator bracket 190 also includes a linear actuator 192. This actuator (e.g., piezoelectric actuator) is operative to displace the link bar 180. That is, the linear actuator is operative to apply a controlled linear displacement to the link bar 180. This linear movement is translated from the link bar through the fixture 162 to the shaft 110. This results in the controlled linear displacement of the shaft 110 (advancement and/or retraction), the supported cradle 40 and probe 10. Such functionality permits vibrating or pulsing the probe relative to patient tissue to impart vibrations therein. Such functionality is important for many elastography ultrasound modalities, as more fully discussed herein.

Figure 4D:
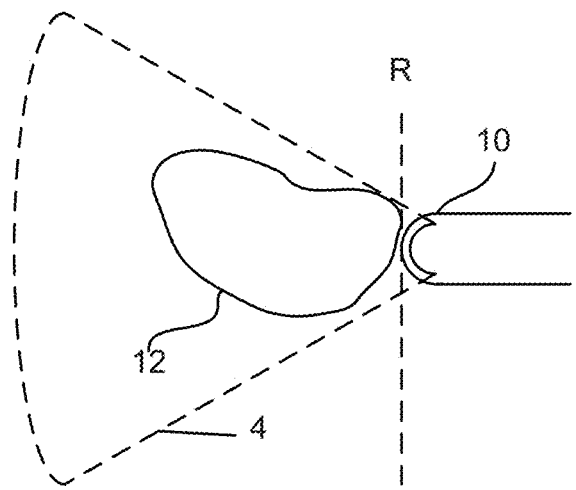
FIGS. 4D-4F illustrate advancement and retraction of a probe supported by a positioning device.
Figure 4E:
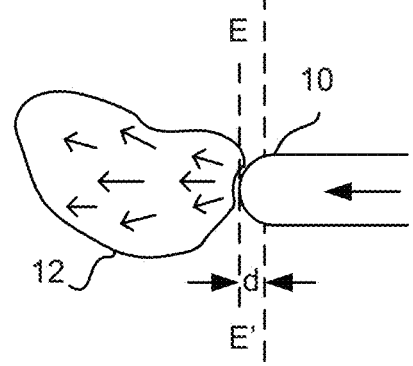
Figure 4F:
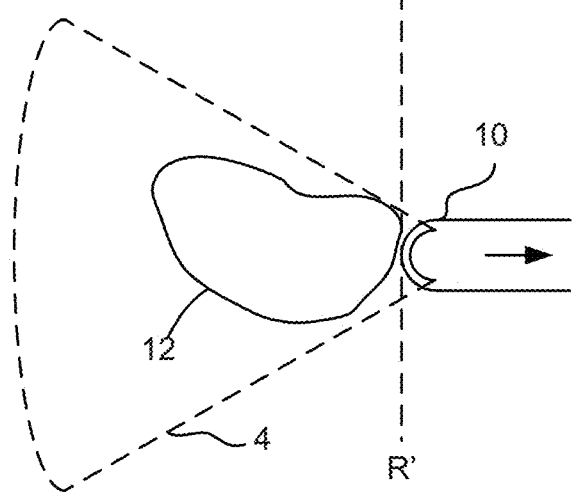

FIG. 4D-4F illustrates the advancement and retraction of an end-fire probe. As shown, the probe 10 may initially be positioned relative to a target tissue (e.g., prostate 12). Once positioned, a first image plane 4 may be acquired. See FIG. 4D. After acquiring an image, the ultrasound probe may be advanced from an initial reference position (R-R') to an extended position (E-E'). That is, the probe may be advanced or pulsed a distance 'd'. See FIG. 4E. For instance, the linear actuator 192 may advance the rotating shaft 100 to displace the tip of the probe 10. The advancement of the probe excites or displaces the tissue 12 imparting a vibration therein. In the presented arrangement, the probe may then be retracted from the extended position to its original reference position. See FIG. 4F. For small displacements, elasticity of the tissue allows the tissue to relax to its original orientation in conjunction with the retraction of the probe. Accordingly, a second image plane is acquired once the probe is retracted to the reference position. Due to the relaxation of the tissue, the tissue of the second image plane is in an identical or near identical orientation relative to the tissue orientation of the first image plane. That is, the two images are taken from the same position and have the same frame of reference (i.e., the images are mechanically registered). The two image planes may be utilized to provide elastographic information of the imaged tissue. It will be appreciated that different tissue may require different displacements or displacement frequencies to produce desired vibration within the tissue. Typically, the displacement will be between about 0.5 mm and about 2 mm. However, other displacements are possible. Further, the tissue may be displaced multiple times for each probe position (e.g., angular position) to provide improved image information.

In summary, when the cradle and probe are attached to the positioning device, the probe is held by the last linkage arm of the device having set of position sensors. These position sensors are connected to the image registration system 2 via an embedded system interface. Hence, the computer has real-time information of the location and orientation of the probe 10 in reference to a unified rectangular or Cartesian (x, y, z) coordinate system. With the dimensions of the probe 10 taken into the calculations, the 3D orientations of the 2D image planes acquired by the probe are known. The ultrasound probe 10 sends signal to the imaging registration 2 (e.g., FIG. 1), which may be connected to the same computer (e.g., via a video image grabber) as the output of the position sensors. The image registration system/computer therefore has real-time 2D images of the scanning area in memory. The image coordinate system and the arm coordinate system are unified by a transformation. Using the acquired 2D images, a prostate surface (e.g., 3D model of the organ) may be generated and displayed on a display screen in real-time.

Figure 5:
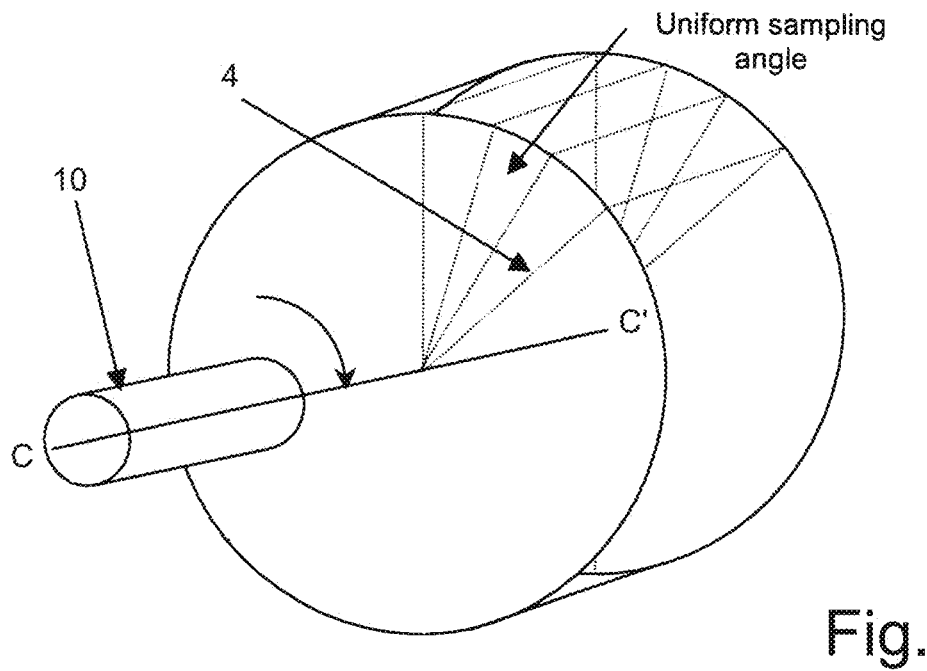
FIG. 5 illustrates acquisition of ultrasound image planes about a fixed rotational axis.

A further benefit of the positioning device is the ability to acquire a first set of images during a first scan (e.g., during a first rotation of the probe about axis C-C') and acquire a second set of images acquires (e.g., during a second rotation of the probe about axis C-C') such that corresponding images of the two image sets are acquired at common angular orientations. For instance, FIG. 5 illustrate the acquisition portion of a side-fire probe 10 secured such that it rotates about a fixed axis of rotation C-C'. When utilizing a motorized positioning device 100, a motor controllably rotates the cradle and probe 40 such that images/image planes 4 may be acquired having, for example, a uniform sampling angle. By way of example, if the motor rotates the probe 10 rotates over 180°, an image may be acquired at a uniform spacing of every 5° (or other uniform spacing) to acquire a first set of ultrasound images. At such time, the probe may return to its initial position and re-rotate over the same 180° to acquire a second set of ultrasound images having the same uniform spacing. That is, the probe may re-image the patient tissue during a subsequent imaging procedure, which may be performed using a second imaging modality. In such an arrangement, corresponding images of the two image sets may scan the same/identical patient tissue. Accordingly, image quality may be improved during subsequent registration of the two sets of images (e.g., registration of corresponding images and/or registration of 3D images produced from each image set).

In the illustrated embodiment, the acquisition portion 6 of the probe 10 is cylindrical or nearly cylindrical. This provides a further benefit when re-imaging patient tissue. Specifically, once the probe is positioned proximate to patient tissue, rotation of the probe does not further distort the patient tissue. In the case of trans-rectal ultrasound, after the acquisition portion 6 of the probe is inserted into the rectum of the patient, subsequent rotation of the acquisition portion 6 does not further distort the prostate gland. The prostate is identical in all image planes though the image planes are angularly offset.

Figure 6:
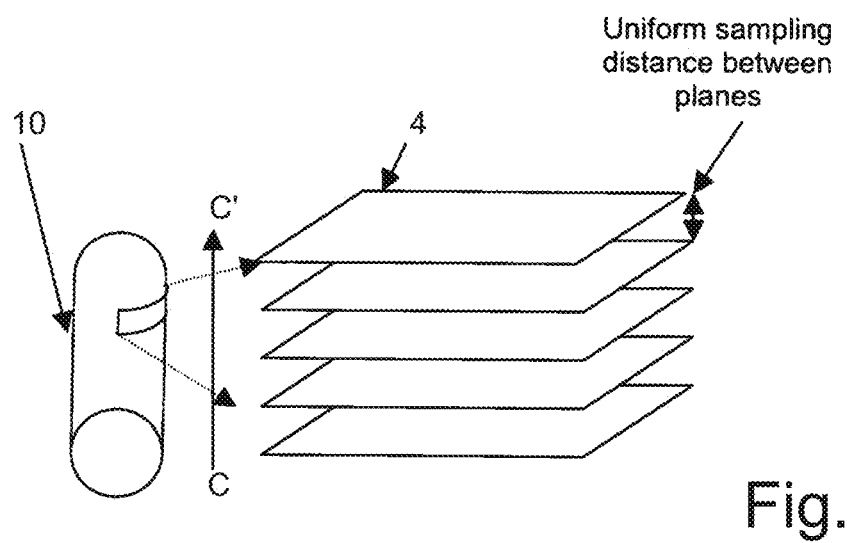
FIG. 6 illustrates acquisition of ultrasound image planes about a fixed linear axis.

Though the positioning devices discussed herein are illustrated as limiting movement about a rotational axis, it will be appreciated that other positioning devices may be utilized. For instance, in some applications (e.g., external applications), a positioning device that limits movement to a linear axis may be desirable. See, e.g., FIG. 6.

The image registration system/computer runs application software and computer programs which can be used to control the system components (e.g., control rotation of the probe during different imaging modalities), provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software represents a computer program product usable with a programmable computer processor having computer-readable program code embodied therein. The software may contain one or more programming modules, subroutines, computer links, and compilations of executable code, which perform the functions of the image registration system. The user interacts with the software via keyboard, mouse, voice recognition, and other user-interface devices (e.g., user I/O devices) connected to the computer system.

While standard B-mode TRUS is a relatively easy and low cost method of generating real-time images and identifying structures of interest, several shortcomings exist. For instance, some malignant cells and/or cancers may be isoechoic to standard B-mode ultrasound. That is, the difference between malignant cells and healthy surrounding tissue may not be apparent or otherwise discernable in a B-mode ultrasound image. Further, speckle and shadows in ultrasound images may make images difficult to interpret. Stated otherwise, standard ultrasound may not, in some instances, provide detailed enough image information to identify tissue or regions of interest.

Other ultrasound imaging modalities may provide significant clinical value, overcoming some of these difficulties. In particular, such modalities may expose tissues or cancers that are isoechoic in standard B-mode TRUS, and therefore indistinguishable from normal tissue in standard ultrasound imaging.

The disclosed system allows for readily registering images acquired from different ultrasound imaging modalities into a single multi-parametric ultrasound image (mpUS image). If the differing modalities are obtained during a single procedure without intervening patient movement, the different modalities of ultrasound images may be obtained in a common frame of reference (FOR). That is, images acquired using different ultrasound modes may be acquired for the patient while the patient is in a single position such that they are mechanically registered. That is, the probe may be rotated a first time in a first imaging modality, then re-rotated in a different imaging modality one or more additional times. In this regard, one or more ultrasound image modalities, obtained from separate scans during a common procedure are mechanically registered. However, slight movement between images may be accounted for using additional software registration if necessary.

Differing Ultrasound Imaging Modalities

A number of different ultrasound imaging modalities are available. However, in some instances, additional external hardware is required to generate the differing modality images. In any modality, ultrasound utilizes sound waves with frequencies which are higher than those audible to humans. Ultrasound images are made by sending pulses of ultrasound into tissue using a probe. The sound echoes and scatters off the tissue; with different tissues boundary reflecting varying degrees of sound, and scatters in different patterns. These reflection and scatter are recorded and displayed as an image.

The most well-known ultrasound modality is a B-mode image, which displays the acoustic impedance of a two-dimensional cross-section of tissue. Other types of image can display blood flow, motion of tissue over time, the location and velocity of blood, the presence of specific molecules, the stiffness of tissue, or the anatomy of a three-dimensional region.

B-Mode is a two-dimensional ultrasound image display composed of bright dots representing the ultrasound echoes. The brightness of each dot is determined by the amplitude of the returned echo signal. That is, a B-mode image is a 2 dimensional cross sectional view of the underlying structures and is made up of hundreds of B-mode (brightness mode) scan lines. These images allow for visualization and quantification of anatomical structures, as well as for the visualization of diagnostic and therapeutic procedures. Lesions such as tumors and atherosclerotic plaques can be identified and the extent of disease burden can be quantified. On a grey scale, high reflectivity (bone surface) is white; low scattering (muscle) is grey and no scattering (water) is black. Deeper structures are displayed on the far-end of probe and superficial structures on the near-end of probe.

Ultrasound elastography (EUS) is a method to assess the mechanical properties of tissue, by applying stress and detecting tissue displacement using ultrasound. EUS is based upon the general principle that stress applied to tissue causes changes which depend on the elastic properties of tissue. There are several EUS techniques depending on the types of stress application and the methods used to detect tissue displacement and construct the image. The main techniques used in the clinical practice include strain EUS, shear wave EUS, transient EUS and acoustic radiation force impulse (ARFI) EUS.

The most commonly used method is strain EUS, also described as compression elastography, sonoelastography (e.g., conventional elastography) is so far the only real-time elastography. The technique is based on low-frequency compression of the tissue, which has previously been manually applied or in some cases using physiological body movement such as respiration or pulsation. In the presented systems and method, the ability to advance and retract the probe to impart movement/vibration in the tissue, as discussed above, allows for acquiring real-time elastography images in a common frame of reference. This is considered novel by itself. The main principle of strain EUS is that a compressive force is applied to tissue causing axial tissue displacement (strain), which is then calculated by comparing the echo sets before and after the compression. Strain EUS provides a qualitative measurement of tissue stiffness contrast. By assuming that the applied stress is uniform, the elastic moduli are inversely proportional to the measured strain (E=stress/strain). Strain is the change in size or shape produced by a system of forces, and it is expressed as a ratio (e.g. the change in length per unit length). The force acting on unit area is known as the stress. Strain EUS is actually measuring the relative strain of one area vs another, and displaying it as a map.

This technique allows direct visualization of the strain contrast information as a image/map ("the elastogram"), which, for visualization purposes, is greyscale or color coded, and is often displayed next to or overlay on top of a B-mode image on the screen. The grey or color scale encoding is chosen by the user. Most often red is used for encoding soft tissues, blue for hard tissues and yellow/green for tissue of intermediate stiffness. The elasticity information derived by this method is qualitative or semi-quantitative. The strain of each area is compared with the remaining tissue within the elastogram, so the elastogram is a relative image available for visual comparison only. The semi-quantitative measurement method includes the ratio of the relative strains between the area of interest and a reference area (usually fat). Strain EUS is applied in the field of oncology imaging to detect and differentiate malignancy in tissue.

Shear wave EUS is based on fact that shear wave speed in soft tissue is related with its stiffness. In a simplified model, the relationship between shear wave speed and Young's modulus can be considered linearly. Supersonic Shear waves are generated by moving focus point at supersonic speed along scan line. Shear waves propagate perpendicularly to the axial displacement caused by the ultrasound pulse and attenuate approximately 10 000 times more rapidly than conventional ultrasound. By use of ultrafast acquisition, the velocity of shear waves can be measured and used to evaluate tissue stiffness by calculating the elastic Young's modulus using simplified model. This technique results in quantitative color coded elastogram.

Conventional elastography is real-time image but with qualitative result. Shear wave Elastography has quantitative result but needs much longer acquisition time for each frame. Considering number of frames to form 3D volume, real-time modalities such as conventional elastography or contrast enhanced US are more feasible for an initial mpUS 3D scan. Once a suspicion region is identified, shear wave elastography may be utilized to rescan identified area to get more reliable and quantitative images. Quantitative images is more useful in terms of lesion classification. Such a would require multi-modality 3D image registration, which gives very high image position requirement.

Acoustic radiation force impulse (ARFI) is another type of shear wave EUS whereby tissue is excited internally by one strong ultrasound pulse, instead of continuous acoustic push as Supersonic does. As the ultrasound pulse travels through the tissue, soft tissue is pushed away from original position. After the excitation and displacement by the pulse, the tissue relaxes to its original configuration. During this procedure, tissue vibration generates shear wave that propagate in perpendicular direction of the ultrasound plus. The propagation of shear wave can be measured using the application of several short-time pulse echoes, which provides propagation speed of shearwave that is related with tissue stiffness. The technique therefore results in a quantitative and repeatable color-coded or greyscale elastogram depicting tissue stiffness. This method has the advantage of imaging deeper tissue, not accessible by superficial external compression. Unlike Supersonic EUS which forms image gradually, ARFI represents image right after one pulse.

Apart from ARFI and Supersonic, transient EUS is also based on shear wave, but use external vibration to excite tissue shear wave. For this modality, external compression is applied by using a short-tone burst of vibration. The method also relies on the estimation of the velocity of shear waves in tissue, but in order to avoid the bias caused by reflections and interferences occurring between the tissues, vibration is transient, so that forward waves can be separated from the reflected waves.

MicroBubble or contrast-enhanced ultrasound (CEUS) is the application of ultrasound contrast medium to traditional medical ultrasound (e.g., B-mode). Ultrasound contrast agents rely on the different ways in which sound waves are reflected from interfaces between substances. This may be the surface of a small air bubble or a more complex structure. Contrast media are gas-filled microbubbles that are administered intravenously to the systemic circulation. For instance, in a prostate application, a small bolus of contrast media/microbubbles may be intravenously injected 130 into a vein associated with the prostate to perfuse the prostate tissue with contrast media prior to imaging. See, e.g., FIG. 1. Microbubbles have a high ability of echogenicity (the ability of an object to reflect ultrasound waves). There is a great difference in acoustic impedance between the gas in the microbubbles and the soft tissue surroundings of the body. Thus, ultrasonic imaging using microbubble contrast agents enhances the ultrasound backscatter of the ultrasound waves, to produce a sonogram with increased contrast due to the high echogenicity difference. Contrast-enhanced ultrasound can be used to image blood perfusion in organs and/or measure blood flow rate in tissue and organs.

There are a variety of microbubbles contrast agents. Microbubbles differ in their shell makeup, gas core makeup, and whether or not they are targeted. Regardless of the shell or gas core composition, microbubble size is fairly uniform. They lie within a range of 1-4 micrometers in diameter. That makes them smaller than red blood cells, which allows them to flow easily through the circulation as well as the microcirculation.

There are two forms of contrast-enhanced ultrasound, untargeted (used in the clinic today) and targeted (under preclinical development). The two methods slightly differ from each other. Untargeted microbubbles are injected intravenously into the systemic circulation in a small bolus. The microbubbles will remain in the systemic circulation for a certain period of time. During that time, ultrasound waves are directed on the area of interest. Targeted contrast-enhanced ultrasound works in a similar fashion, with a few alterations. Microbubbles targeted with ligands that bind certain molecular markers that are expressed by the area of imaging interest are still injected systemically in a small bolus. Microbubbles travel through the circulatory system, eventually finding their respective targets and binding specifically. Ultrasound waves can then be directed on the area of interest. Detection of bound microbubbles may then show that the area of interest is expressing that particular molecular marker, which can be indicative of a certain disease state, or identify particular cells in the area of interest.

Apart from diagnostic usage, microbubbles can be used in treatment as well. They can be used to carry drugs for site-specific treatment. For microbubbles, the US energy needed for cavitation is very small. This enables the use of medical US to collapse microbubbles and allow their carried drug to release in areas of interest. Cavitation of microbubbles also helps absorption of released therapeutic agent as the collapsing energy in capillary beds can increases capillary permeability.

Doppler ultrasound uses frequency shift of reflected sound waves to see tissue motion, especially the blood flows through a blood vessel. It helps users evaluate blood flow through arteries and veins. During Doppler ultrasound, the movement of blood cells causes a change in frequency of the reflected sound waves (called the Doppler Effect). If there is no blood flow, the frequency shift does not happen. Information from the reflected sound waves can be processed by a computer to provide graphs or pictures that represent the speed and direction of blood flow. Cancerous tissue typically has differing blood flow characteristics than healthy tissue allowing differentiation of the same. There are several kinds of Doppler ultrasound including color Doppler, pulsed Doppler and power Doppler. Any of these modalities may be utilized.

Photoacoustic tomography (PAT), or Photoacoustic computed tomography (PACT), is an ultrasound analysis technique based on the reconstruction of an internal photoacoustic source distribution from measurements acquired by scanning ultrasound detectors over a surface that encloses the source under study.

The PAT source is produced inside the tissue by the thermal expansion that results from a small temperature rise, which is caused by the absorption of externally applied radiation of pulsed electromagnetic (EM) waves. PAT is also called optoacoustic tomography (OAT) or thermoacoustic tomography (TAT), with the term "thermoacoustic" emphasizing the thermal expansion mechanism in the PA generation. OAT refers particularly to light-induced PAT, while TAT is used to refer to rf-induced PAT.

PAT typically involves optical excitation, ultrasonic detection, and image formation. A short-pulsed laser is usually used to produce ultrasound in biological tissue efficiently. The amplitude of the photoacoustic pressure depends on the optical energy deposition as well as the thermal and mechanical properties of the tissue. Because either unscattered or scattered photons can produce photoacoustic signals, photoacoustic waves can be generated deeply in biological tissue. Because the ultrasonic scattering coefficient in tissue is 2-3 orders of magnitude less than the optical counterpart, high spatial resolution can be achieved by detecting the photoacoustic waves. Consequently, PAT allows for high-resolution optical-contrast imaging.

Generating mpUS Image

Figure 7A:
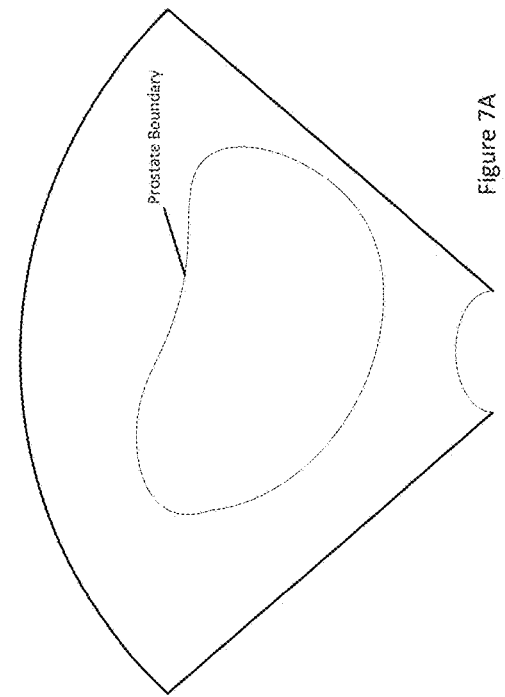
FIGS. 7A-7C illustrate simplified 2D images acquired using different ultrasound modalities.
Figure 7B:
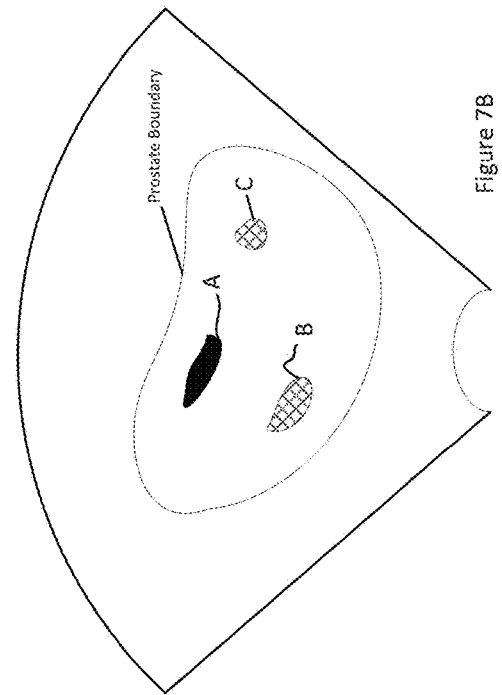
Figure 7C:
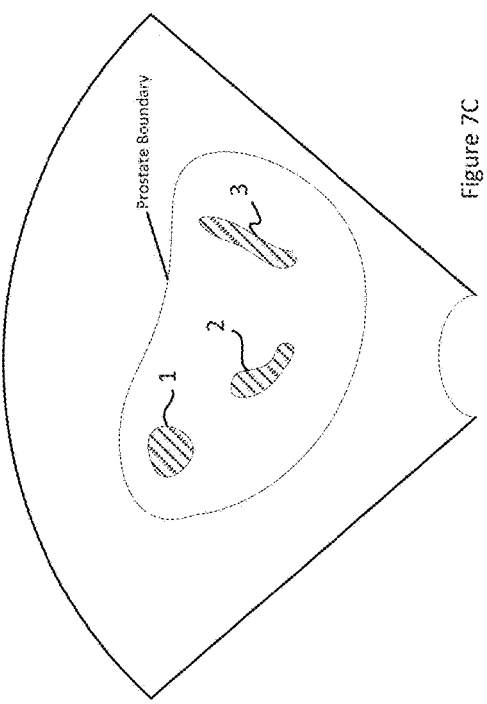
Figure 7D:
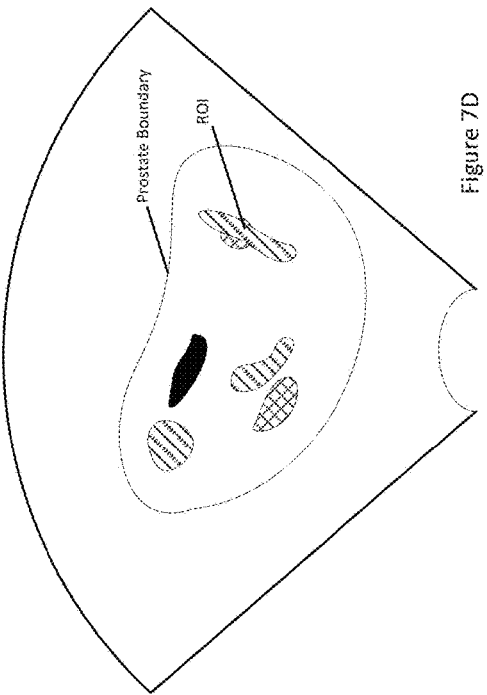
FIG. 7D illustrates a mpUS generated via registration of the images of FIGS. 7A-7C.

When the probe is utilized in conjunction with the positioning device, two or more sets of different ultrasound modalities images may be registered to generate a series of 2D mpUS and/or a 3D mpUS volume. FIGS. 7A-7D illustrate highly simplified ultrasound images for three ultrasound imaging modalities (FIGS. 7A-7C) and a mpUS image (FIG. 7D) generated from the three ultrasound imaging modalities. Each of the illustrated images is a 2D image for purposes of simplification. However, it will be appreciated that 3D images/volumes may be utilized as well. As shown in FIG. 7A, in a first rotational scan a standard B-Mode ultrasound image is acquired. In the present example, the image is of a patient's prostate. After the first image set is acquired, the probe is re-rotated using a second imagining modality. In the present example, an elastography ultrasound is performed during the second scan. See FIG. 7B. As shown in the exemplary scan, a number of areas in the scan (A, B and C) having an elasticity above or below a predetermined threshold are illustrated. After the elastography image is obtained, the probe may again be re-rotated using a third imaging modality. In the present example, a Doppler image is performed during the third scan to identify areas (1, 2 and 3) of blood flow above or below a predetermined threshold. Additional or different scans may be performed. FIG. 7D illustrates the registration of the three images into a mpUS image. This image with multiple modes of information may then be analyzed to identify potential regions of interest.

In one arrangement, a user may manually analyze one or more mpUS images to identify regions of interest in each mpUS image. In this regard, the use of, for example, a standard b-mode image with a registered elastography image and registered Doppler image may allow the user to better identify tissues regions of interest, for instance, based on the user's experience. Upon identifying such a region(s) (e.g., overlap of elastography area C with Doppler area 3), the identified region(s) may be saved by the system. The system may then be used to align the probe with the region of interest to provide a real-time image including the identified region of interest. Accordingly, such a real-time image may be utilized to guide a needle or other therapy applicator to the point of interest.

Figure 8A:
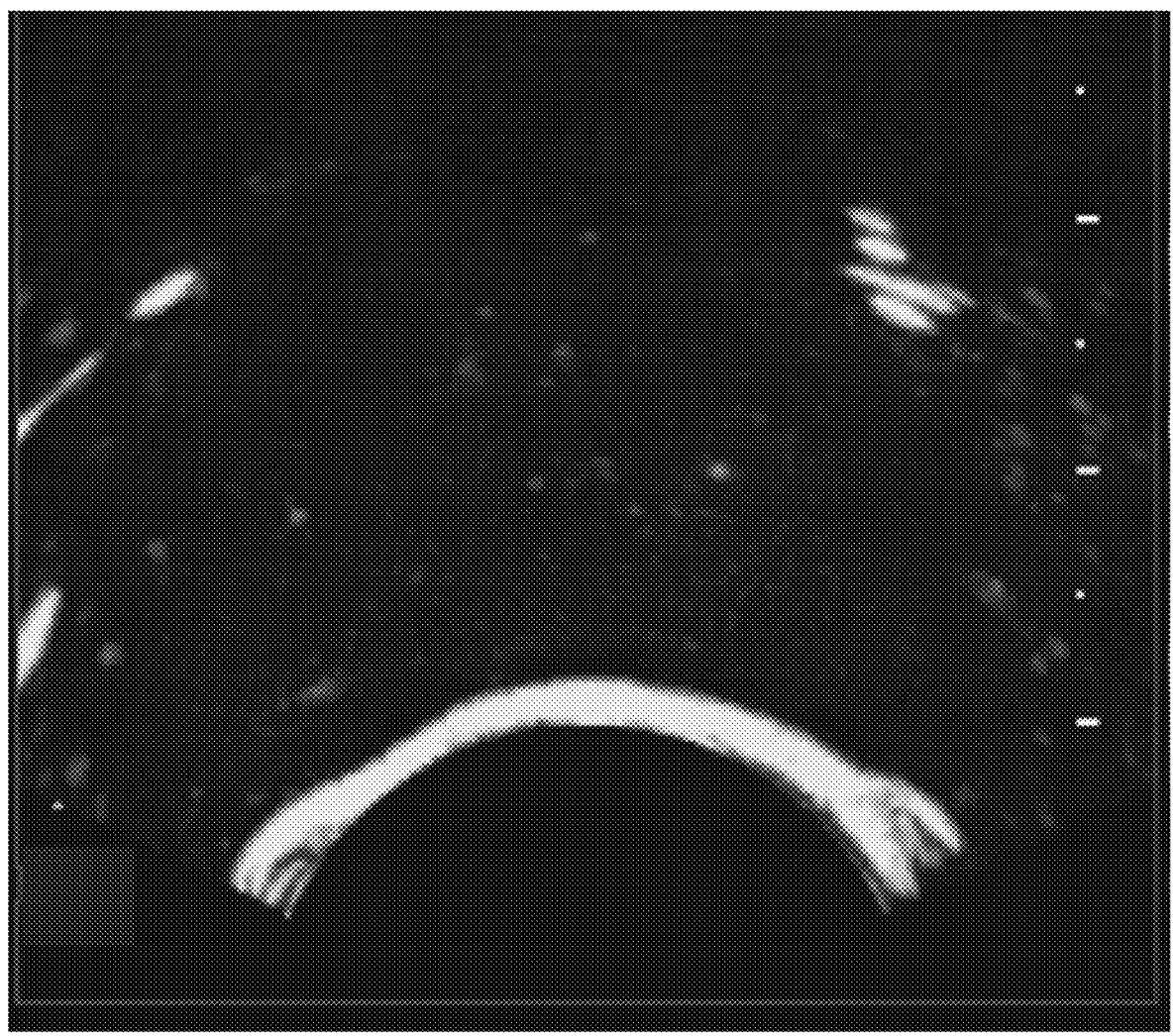
FIGS. 8A-8C illustrate 2D ultrasound images acquired using different ultrasound modalities.
Figure 8B:
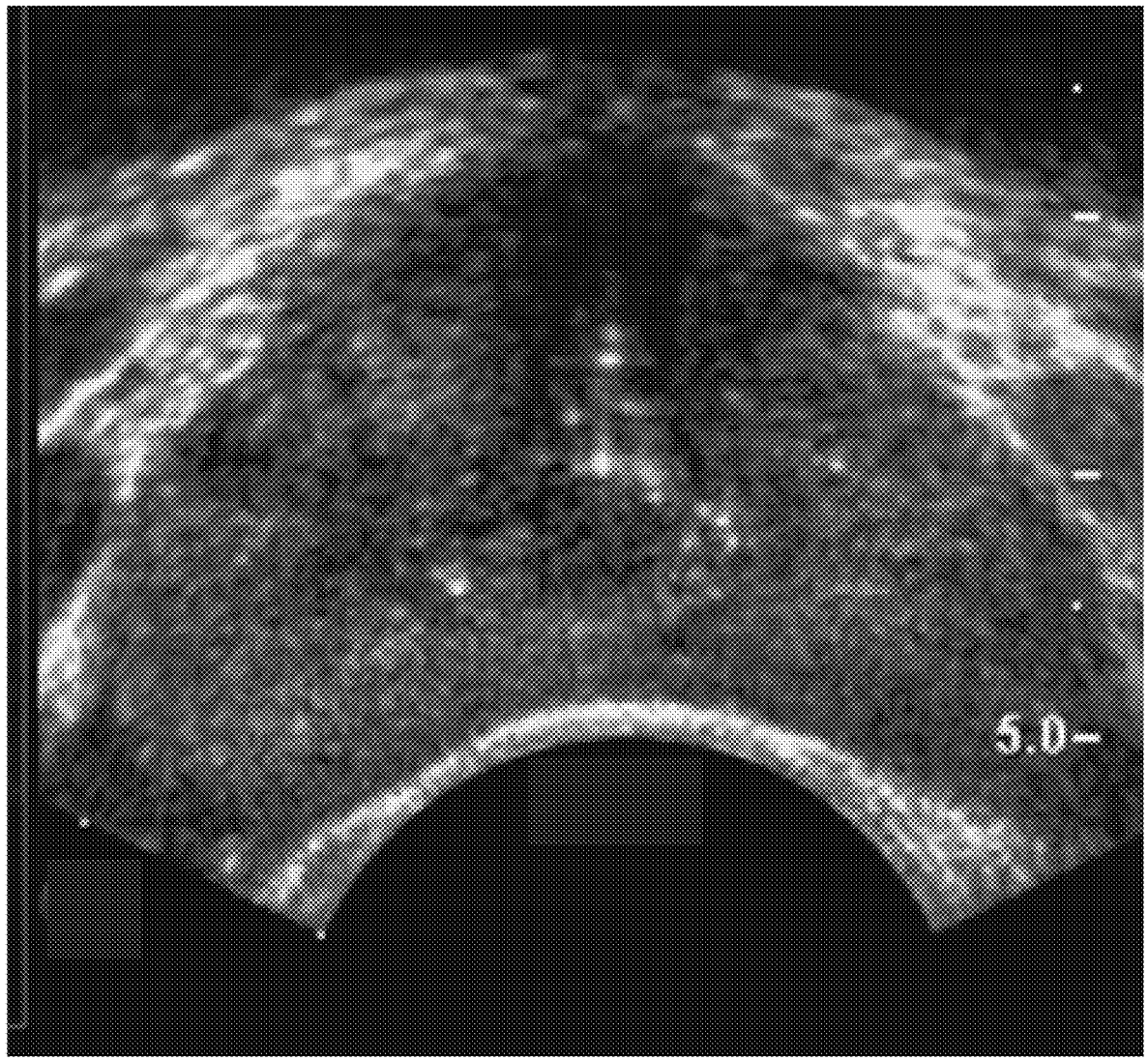
Figure 8C:
Figure 8D:
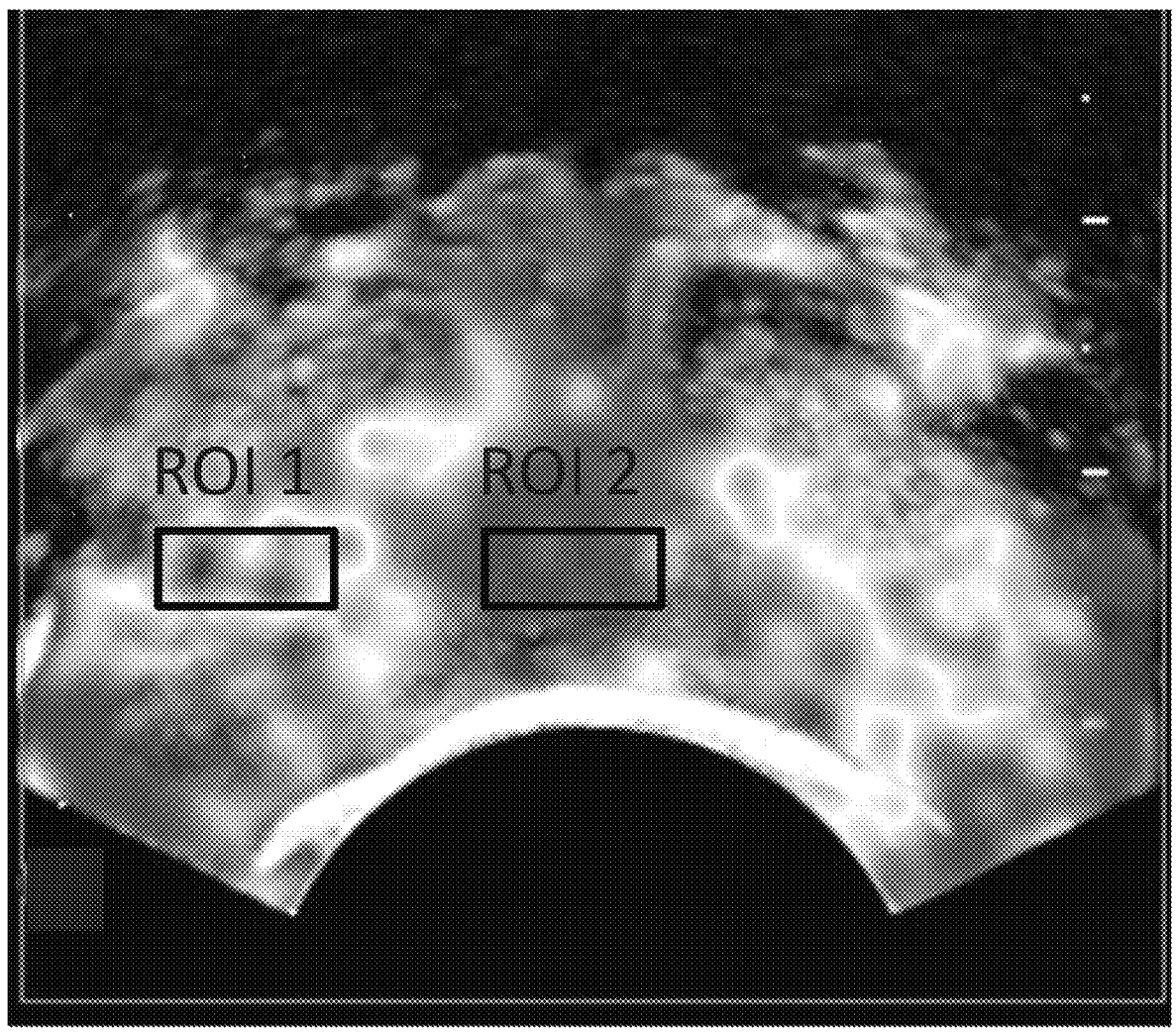
FIG. 8D illustrates a mpUS image generated via registration of the images of FIGS. 8A-8C.

FIGS. 8A-8C illustrate ultrasound images taken utilizing three separate ultrasound imaging modalities. These images are registered to generate a mpUS image as shown in FIG. 8D. The three imaging modalities illustrated in FIGS. 8A-8C are B-mode ultrasound imaging (FIG. 8A), elastography ultrasound imaging (FIG. 8B) and contrast enhanced ultrasound (CEUS) imaging or microbubble ultrasound imaging (FIG. 8C). It is currently believed that these three ultrasound imaging modalities generate a composite image that favorably corresponds to a Magnetic Resonance (MR) image. Along these lines, the B-mode image of FIG. 8A is generally equivalent to a T2 contrast MR image. The B-mode image, like a T2 contrast MR image, primarily shows anatomical features. The elastography image of FIG. 8B is equivalent to a diffusion weighted contrast MR image, which provides density information for the imaged tissue. The CUES image of FIG. 8C is a B-mode ultrasound image acquired after the injection of a contrast agent to the imaged tissue. The CUES image is an equivalent to dynamic contrast in a MR image, which provides a measure of angiogenesis or blood flow in tissue. As shown, each of these images (i.e., FIGS. 8A-8C) show an identical image planes of a portion of patient tissue acquired by an ultrasound transducer. That is, while these images are acquired in subsequent scans, these images show the identical tissue and are therefore readily registered together (e.g., as 2D images or as 3D images). The registration of these three images results in the mpUS image shown in FIG. 8D. As shown, the composite image provides a rich set of tissue data for subsequent analysis. Stated otherwise, the acquisition of identical images that are readily registered together allows for generating an image with tissue data that approximates the tissue data in an MR image.

Figure 9A:
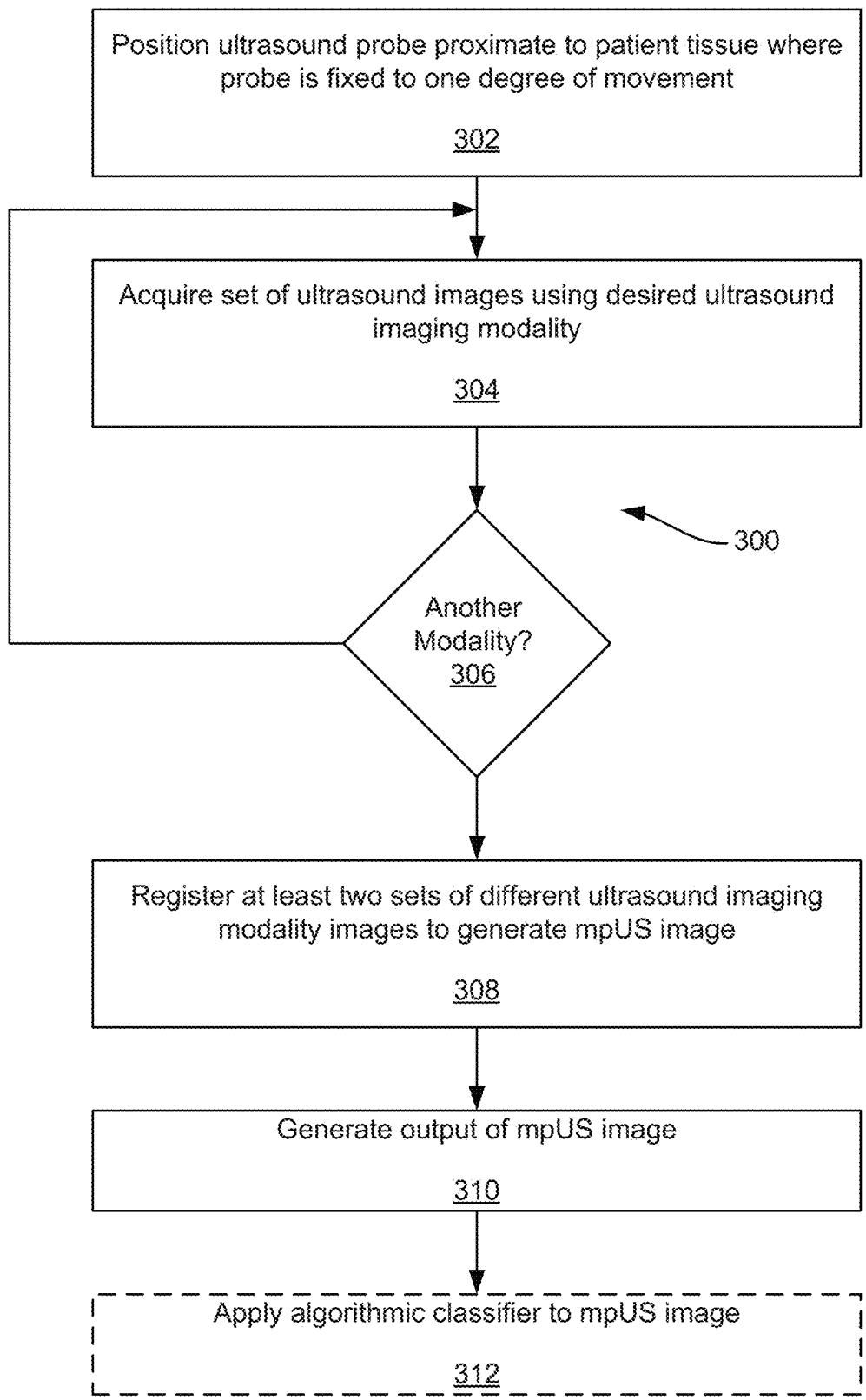
FIGS. 9A-9C illustrate three processes for generating muUS images.
Figure 9B:
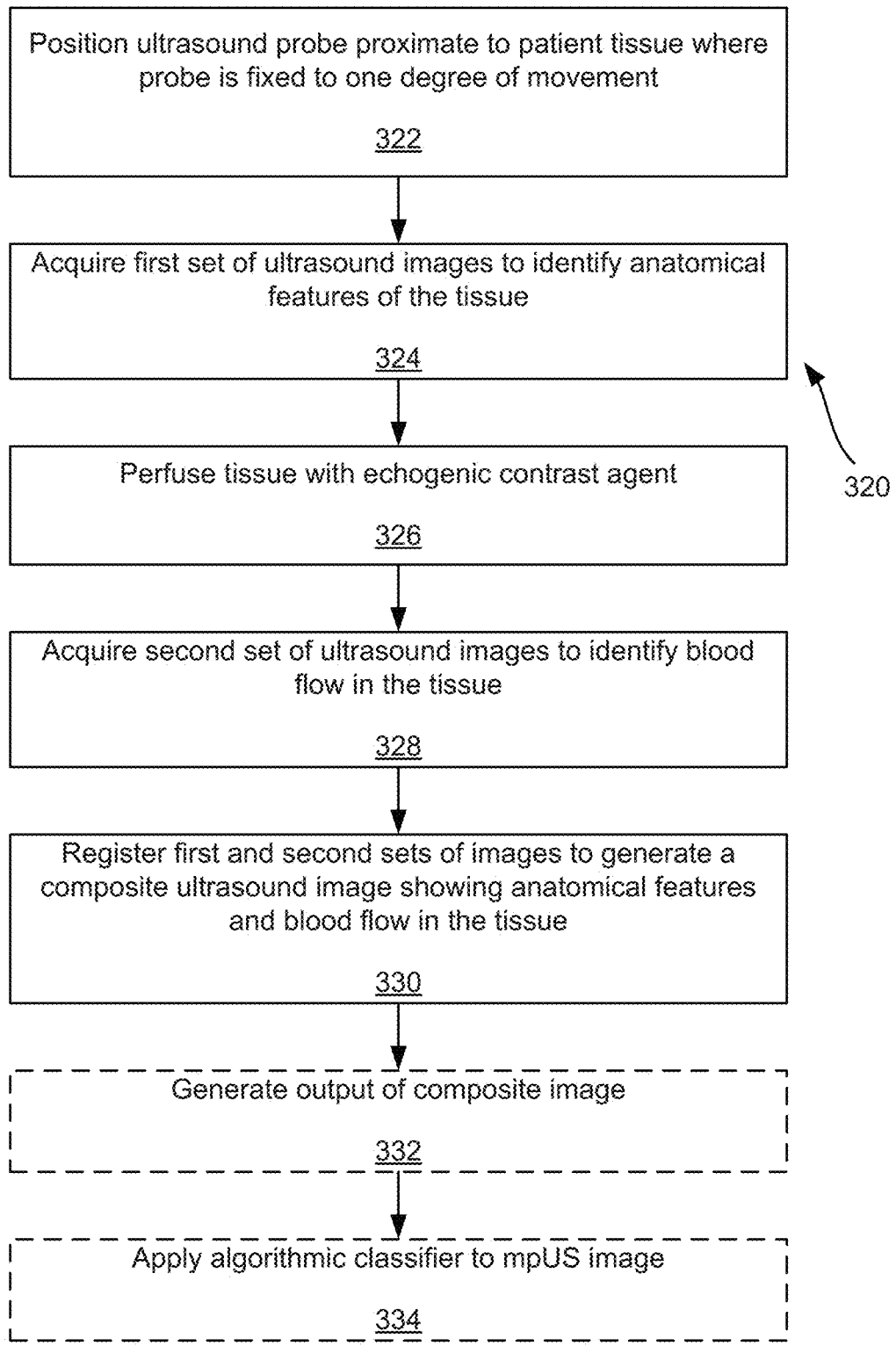
Figure 9C:
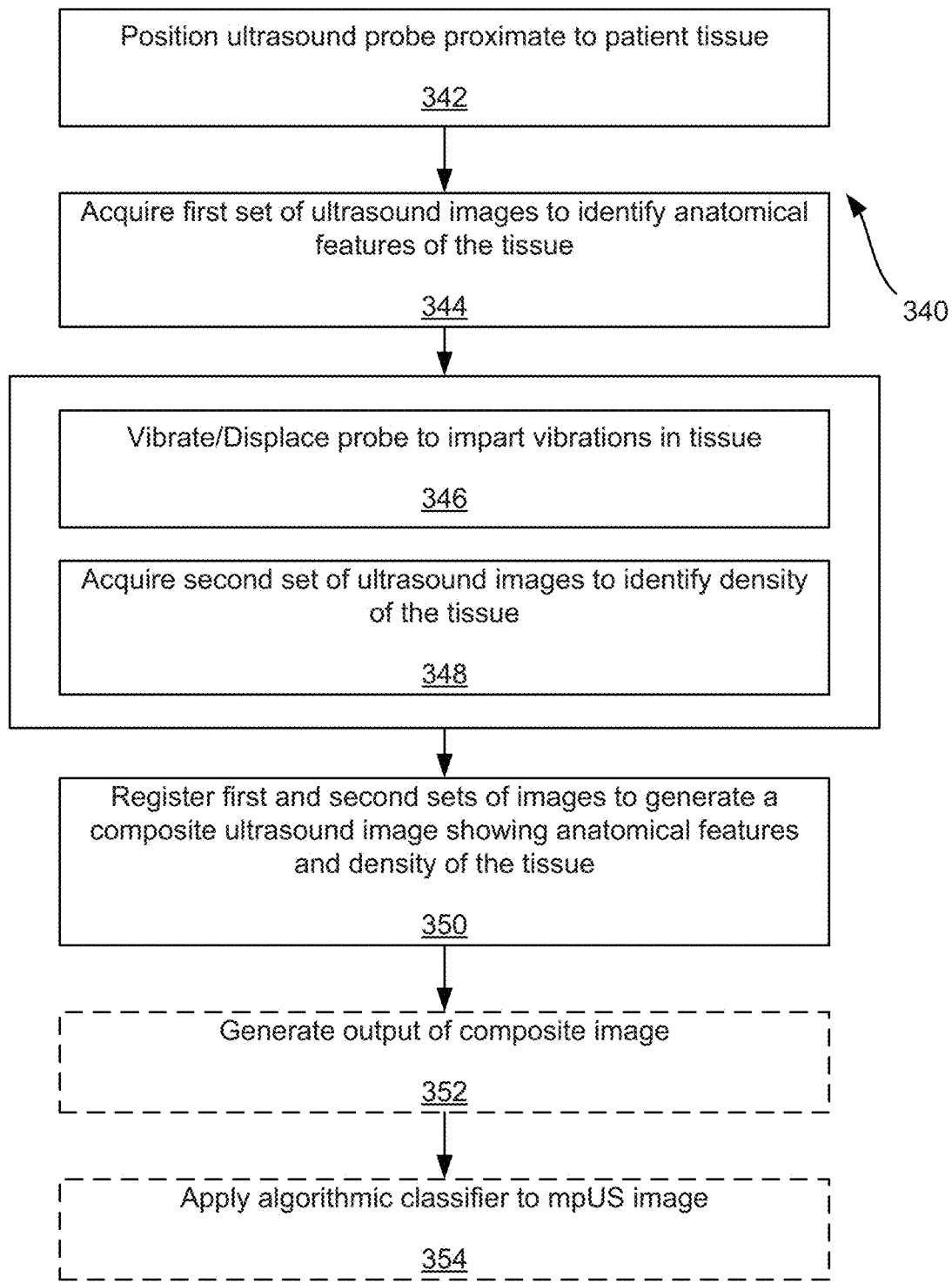

FIGS. 9A-9C illustrate three processes for generating mpUS images (e.g., composite ultrasound images). Specifically, FIG. 9A illustrates a process 300 for sequentially acquiring different modality ultrasound images and registering these images into a common frame of reference. Initially, an ultrasound probe is positioned 302 proximate to patient tissue. Typically the probe is fixed to one degree of movement (e.g., rotational movement about an axis). Once positioned, a set of ultrasound images may be acquired 304 utilizing desired ultrasound imaging modality. A determination 306 is made if another modality is desired. If so, step 304 may be repeated one or more times using different ultrasound modalities and/or introducing vibration into the tissue and/or perfusing the tissue with a contrast agent. Once at least two sets of different ultrasound imaging modality images are acquired, these different sets of images are registered 308 to generate a multi-parameter/composite ultrasound image. This image may be output 310 to user display and/or may be algorithmically classified 312 to identify one or more regions of interest.

FIG. 9B illustrates a process 320 for generating a composite ultrasound image including anatomical features of tissue and blood flow in that tissue. Initially, an ultrasound probe is positioned 322 proximate to patient tissue. A first set of ultrasound images are acquired 324 identifying anatomical features of the tissue. The tissue is then perfused 326 with an echogenic contrast agent. Once perfused, a second set of ultrasound images are acquired 328 which identify blood flow within the tissue. The first and second sets of ultrasound images are registered 330 to generate a composite ultrasound image shown anatomical features and blood flow within the tissue. The composite image may be output 332 to a display and or algorithmically classified 334.

FIG. 9C illustrates a process 340 for generating a composite ultrasound image including anatomical features of tissue and the density of that tissue. Initially, an ultrasound probe is positioned 342 proximate to patient tissue. A first set of ultrasound images are acquired 344 identifying anatomical features of the tissue. A second set of ultrasound images are acquired 348 in conjunction with vibration/displacement 346 of the probe to impart vibrations within the tissue contacted by the probe. As noted above the images are preferably taken at a common reference location between vibrations. Once first and second set of images are acquired, they are registered 350 generate a composite ultrasound image showing anatomical features and density of the tissue. The composite image may be output 352 to a display and or algorithmically classified 354.

The composite image and/or the individual images may be analyzed (e.g., manually or via algorithm) to identify one or more regions of interest (ROI). In one embodiment, one or more points of interest or regions of interest (ROI) may be automatically identified using the mpUS image. As noted, the mpUS image(s) contains a rich set of tissue data that facilitate algorithmic analysis. That is, an algorithm or classifier may be utilized to identify regions of interest.

Classifier algorithm information collection initially entails the imaging of tissues having regions known to be cancerous or otherwise of interest (e.g., lesions) using the different imaging modalities for classification. In this regard, images for each modality may be taken of tissues (e.g., prostates) having known cancerous regions/lesions for a large group of patients. The images are collected and used to compile a database of images having known cancerous regions. Once the images are collected for each imaging modality, histological data for the imaged tissue may be acquired. That is, histological slices from the actual imaged tissues (e.g., prostates) corresponding to the 2D and/or 3D images may be obtained. Such histological data may entail a histologist examining and/or testing the histological slices and labeling the slices and corresponding images with pertinent information to generate ground truth images. The ground truth images for each modality are all mapped to a common frame of reference and may each contain markers that identify/label every location of the image (e.g., prostate) as cancerous, non-cancerous or otherwise. Further, the type of cancer may also be labeled.

The database of images whose cancer/lesion characteristics are known is referred to as ground truth images. The ground truth images may be utilized to identify correlations between the image data and the known cancerous tissue and non-cancerous tissue. For instance, image intensity, blood flow, elasticity etc. may be correlated to the existence of cancerous tissue. Such correlations may be identified individually for each imaging modality. Furthermore, correlations between known tissue types and combinations of any two or more of the imaging modalities may be identified. For example, the correlations between tissue types and an mpUS image formed of B-mode images and elastography images may be identified. By way of example only, tissue with intensity above/below a predetermined threshold and with an elasticity above/below a predetermined threshold may indicate potentially cancerous tissue. Accordingly, these correlations may be subsequently utilized during multimodal imaging to classify tissue in real-time or near real-time images. That is, if areas in the currently imaged tissue have predetermined correlations, these regions may be identified (e.g., automatically) as cancerous or otherwise of interest. In any case, once training images and histological data is obtained for a set of ground truth images, correlations may be identified for the different modalities or different combinations of the modalities.

The generation of correlations or classifiers is initially performed in an offline model training system. See FIG. 10. In the illustrated embodiment, the offline training model utilizes mpUS images for training. However, it will be appreciated that individual image modalities may likewise be classified. Inputs to the system include mpUS ultrasound images of tissue having known histological data. The histology data and the ultrasound images in the patient database are used to generate ground truth information used to train a classifier or multiple classifiers (e.g., depending on the combination of imaging modalities). Once ground truth tumor information is generated, regions of interest (ROIs) from different classes of the ground truth information may be identified. For instance, a feature extraction process may be performed on each different class to generate extracted feature vectors. That is, cancerous regions and benign regions in the training images are known. The features to describe different ROIs are extracted. The feature sets then represent each image feature. Also, the best feature sets may be selected through a feature selection procedure. Then such feature vectors from each ROI may be used as inputs in a classifier training process to produce trained classifiers that the multi-parameter ultrasound imaging system may utilize to identify suspect regions in a current mpUS image.

Figure 10:
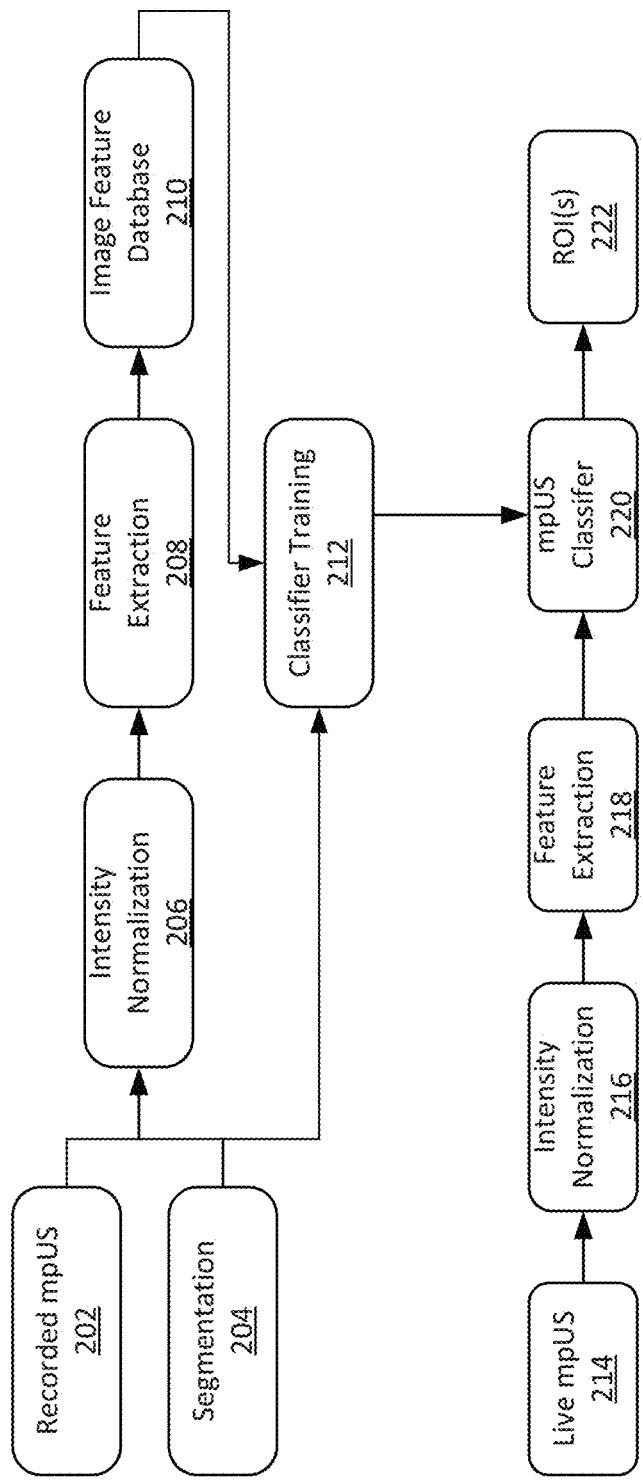
FIG. 10 illustrates a process for training a classifier and a process for utilizing a trained classifier to identify regions of interest (ROIs).

One method for generating tumor ground truth information for ultrasound images (e.g., prostate images) is illustrated in FIG. 10 and can be summarized as follows: initially, in a training dataset of mpUS images 202, the prostate boundary of the 2D images (or 3D volumes sliced into 2D image slices) are segmented 204 by a manual, semi-automatic or automatic segmentation algorithm. Histology data is also incorporated into the 2D images with cancerous/lesion/tumor regions marked out by a histologist or urologists. After this step, the cancerous regions and benign regions (ROIs) in the training images are known. The images may be processed in a intensity normalization process 206. Intensity normalization helps to remove any general brightness in the image and help accentuate the contrast present in the image between the different regions. As different ultrasound machines display the images with different brightness, for classifier training it is more desirable to identify contrast than the true intensity value. Then a set of feature vectors to describe different ROIs is extracted 208 by image processing algorithms. The feature vectors include, without limitation, statistical features, gradient features and Gabor filtering features. The features with the most discriminant power are selected through a feature selection algorithm and saved 210 to an image feature database. As a result, each ROI with known class label is digitized by a feature vector. They are used as training samples to train 212 a classifier. The best parameters associated with a classifier are determined through the training procedure. This is offline model training. For a new patient, the system acquires 214 an mpUS image, normalizes 216 the mpUS image, extracts 218 features from the mpUS image, applies 220 the previously trained classifier and provides 222 initial suggested biopsy or therapy regions (ROIs) in the mpUS image based on the trained classifier. One method of training a classifier is set forth in co-owned U.S. Pat. No. 8,175,350, which is incorporated herein as if set forth in full.

Returning to the example of FIGS. 7A-7D, a trained classifier may be operative to automatically identify an ROI based on an overlap of outlying elastic properties and outlying blood flow properties. It will be appreciated that the trained classifier may be specific to the imaging modalities that form a mpUS image. In any case, such a ROI may be flagged for a user and or saved to the system. In any arrangement, once ROIs are identified, these ROIs may be accessed for biopsy or therapy. Again, such biopsy or therapy may be performed during the same procedure where the images are acquired.

Figure 11:
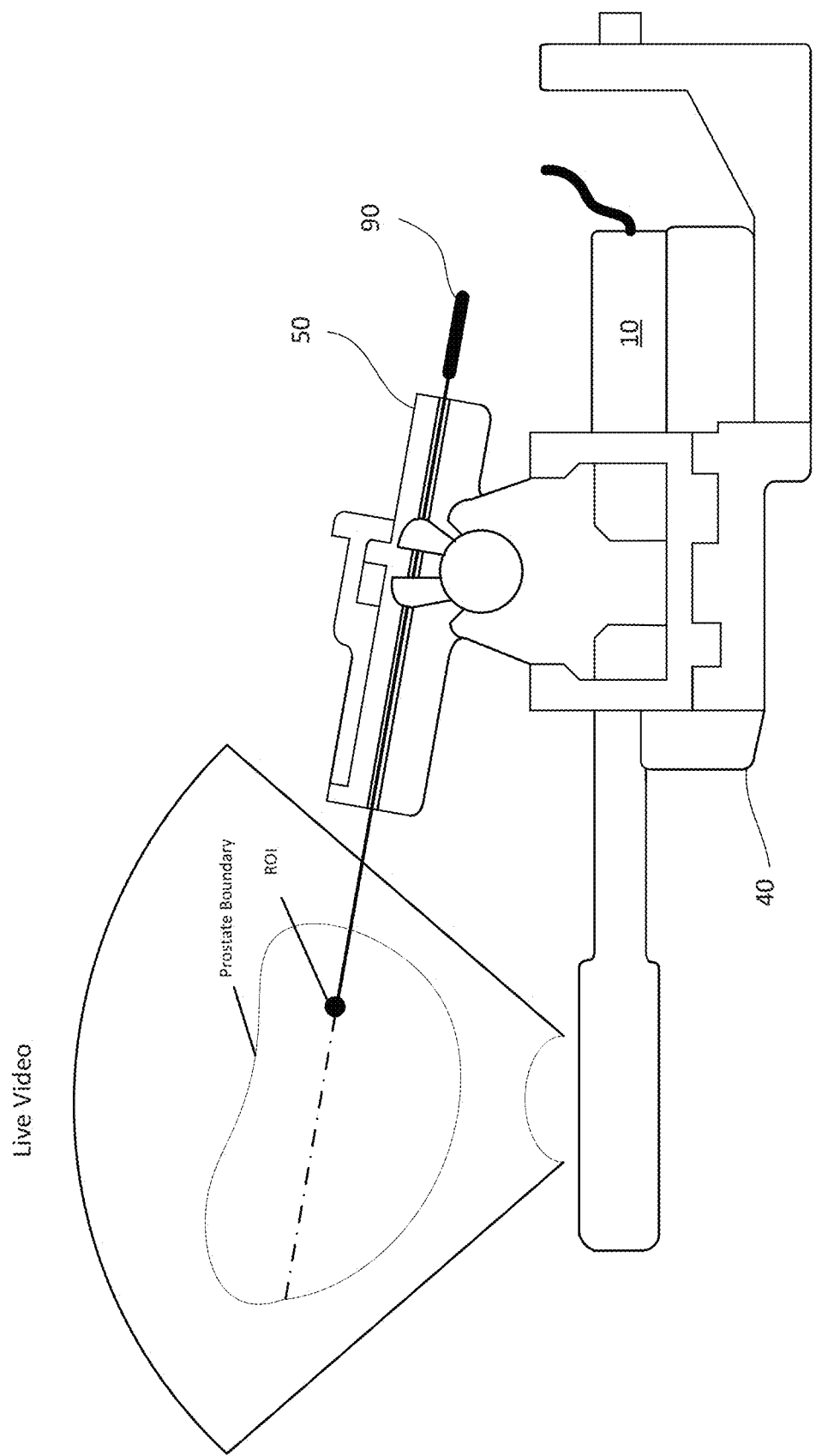
FIG. 11 illustrates targeting a ROI using a mpUS image.
Figure 12:
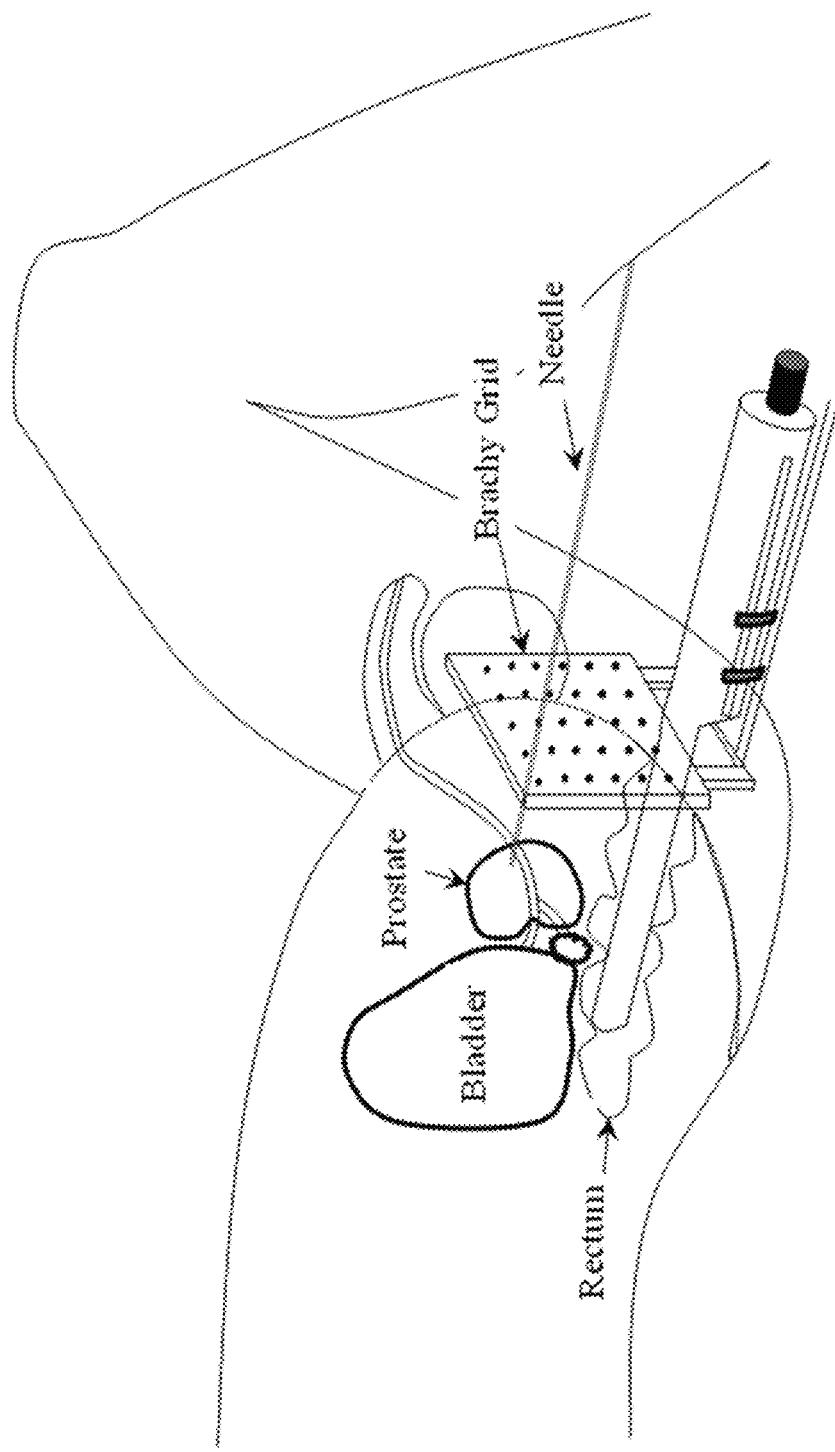
FIG. 12 illustrates using an external grid to target a ROI.

FIG. 11 shows one biopsy therapy device that is incorporated with the probe 10. As shown, a cradle assembly 40, which connects to the positioning system, supports the probe 10 during image acquisition. Such a cradle assembly is set forth in co-pending U.S. patent application Ser. No. 15/203,417, which is incorporated by reference in its entirety. The cradle assembly 40 includes a guide assembly 50, which supports a biopsy needle or therapy delivery trocar 90 within a plane of the probe. Along these lines, once a region of interest is identified, the probe may be rotated to align with the ROI and the guide assembly rotates to align a trajectory of the needle/trocar 90 with the ROI. The needle/trocar may then be advanced to the ROI under real time guidance. See FIG. 10. Of note in FIG. 10, rather than showing a live ultrasound image (e.g., B-mode) registered with the mpUS image, the real-time image simply includes a target point ROI that was identified from the mpUS image. In this example, the system may use a real time image or volume to provide guidance for an introducer (e.g., needle, trocar etc.) of a targeted focal therapy (TFT) device. Such TFT devices typically ablate cancer foci within the prostate using any one of a number of ablative modalities. These modalities include, without limitation, cryotherapy, brachytherapy, targeted seed implantation, high-intensity focused ultrasound therapy (HIFU) and/or photodynamic therapy (PDT). In another arrangement, the needle trocar may be supported by an external system separate from the probe. See FIG. 12.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The invention claimed is:

1. An ultrasound medical imaging system, comprising:
an ultrasound probe;
a positioning device having:
- a linkage with at least two rigid arms, wherein one end of said linkage is a free end that is operative to move in three dimensions and wherein said free end is configured to be locked in a fixed position;
- a rotational shaft interconnected to the free end of said linkage;
- a rotary encoder configured to generate an angular outputs indicative of an angular orientation of said rotational shaft about said rotational axis;
- a vibratory actuator for controllably imparting a vibration in said rotational shaft between a reference position and a displaced position, wherein said vibratory actuator moves said rotational shaft in a non-rotational direction; and
- an ultrasound probe holder attached to said rotational shaft for releasable holding an acquisition array of the ultrasound probe in a known position relative to a rotational axis of said rotational shaft;

an ultrasound system for acquiring a plurality of two-dimensional ultrasound images in conjunction with rotation of said rotational shaft about said rotation axis and vibration of said rotational shaft, wherein each of said plurality of two-dimensional image are acquired while said rotational shaft is in said reference position;

a registration system configured to:
- receive said angular outputs from said rotary encoder;
- receive said plurality of two-dimensional ultrasound images; and
- utilize said angular outputs to register said plurality of two-dimensional ultrasound images into a three-dimensional ultrasound image; and a display configured to display said three-dimensional ultrasound image.

2. The system of claim 1, wherein said vibratory actuator is configured to displace said rotational shaft in a direction substantially aligned with said rotational axis.

3. The system of claim 1, further comprising:
a controller, the controller configured to:
- control said vibratory actuator to displace said rotational shaft; and
- operate said ultrasound to acquire an image while said rotational shaft is at said reference position.

4. The system of claim 1, wherein said vibratory actuator vibrates said rotational shaft between said reference position and said displaced position at a user selectable frequency.

5. The system of claim 1, wherein a distance between said reference position and said displaced position is user selectable.

6. The system of claim 1, further comprising:
a motor for controllably rotating said rotational shaft.

7. The system of claim 6, further comprising:
a controller configured to:
- control said motor to rotate said rotational shaft to a known angular position; and
- operate said ultrasound to acquire an image while said rotational shaft is in said known angular position.

* * * * *